United States Patent
Ohta et al.

(10) Patent No.: US 10,174,333 B2
(45) Date of Patent: Jan. 8, 2019

(54) FUSED GENE, VECTOR, TRANSGENIC PLANT, METHOD FOR MANUFACTURING VEGETABLE FAT OR OIL, METHOD FOR CONSTRUCTING TRANSGENIC PLANT, AND KIT FOR CONSTRUCTING TRANSGENIC PLANT

(71) Applicant: Tokyo Institute of Technology, Tokyo (JP)

(72) Inventors: Hiroyuki Ohta, Tokyo (JP); Mie Shimojima, Tokyo (JP); Yuka Madoka, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 237 days.

(21) Appl. No.: 14/913,521

(22) PCT Filed: Aug. 26, 2014

(86) PCT No.: PCT/JP2014/072296
§ 371 (c)(1),
(2) Date: Feb. 22, 2016

(87) PCT Pub. No.: WO2015/029997
PCT Pub. Date: Mar. 5, 2015

(65) Prior Publication Data
US 2016/0244772 A1    Aug. 25, 2016

(30) Foreign Application Priority Data

Aug. 29, 2013 (JP) ................................. 2013-177774

(51) Int. Cl.
*C12N 15/82* (2006.01)
(52) U.S. Cl.
CPC ..... *C12N 15/8238* (2013.01); *C12N 15/8237* (2013.01); *C12N 15/8247* (2013.01)
(58) Field of Classification Search
None
See application file for complete search history.

(56) References Cited

U.S. PATENT DOCUMENTS

| | | |
|---|---|---|
| 2005/0079471 A1 | 4/2005 | Rogan et al. |
| 2005/0079571 A1 | 4/2005 | Collier et al. |
| 2005/0170478 A1 | 8/2005 | Stymne et al. |
| 2009/0078645 A1 | 3/2009 | Matsui et al. |

FOREIGN PATENT DOCUMENTS

| | | |
|---|---|---|
| JP | 2001-512977 | 8/2001 |
| JP | 2007-104960 A | 4/2007 |
| JP | 2012-007146 | 1/2012 |
| JP | 2012-153833 | 8/2012 |
| JP | 2014-068638 | 4/2014 |
| WO | 98/38295 | 9/1998 |
| WO | 2007049816 | 5/2007 |
| WO | 2008/157226 A2 | 12/2008 |
| WO | 2011156520 | 12/2011 |

OTHER PUBLICATIONS

Kobayashi et al 2009 (The Plant Journal 57: p. 322-331).*
Chang et al 2003 (Theoretical and Applied Genetics 106: p. 269-276).*
Hung et al. 2013 FEBS let.
Sanjaya et al. 2013 Plant Cell.
Peng et al. 2010 Plant Cell Rep.
Kim et al., 2013 FEBS Open Bio.
Lipman and Pearson, Science, 227, 1435(1985).
Delhaize and Randall 1995 Plant Physiology.
Bligh and Dyer, Can. J. Biochem. Physiol, 1959 37, p. 911.
Kobayashi et al. 2004 Plant Phys.
Clough et al., Plant Journal 1998 16:735-743.
M. La Russa et al., Journal of Biotechnology, 2012, 162, 1, 13-20.
Proceedings of the Annual Meeting of the Japanese Society of Plant Physiologists, 2011, 52, 344, PL086 (919).
Iwai et al., Plant Biotechnology Journal, Jul. 2014, 12, 808-819.
Proceedings of the Annual Meeting of the Japanese Society of Plant Physiologists, 2014. 03, 55, 362, PL147 (0872).
International Search Report for PCT/JP2014/072296 dated Oct. 21, 2014.
JP Office Action (JP 2015-534232) dated May 15, 2018 (w/translation), 12 pages.
Jako, Colette et al., "Seed-Specific Over-Expression of an *Arabidopsis* cDNA Encoding a Diacylglycerol Acyltransferase Enhances Seed Oil Content and Seed Weight", Plant Physiology, 126(2):861-874, 2001.
Shimojima, Mie et al., "An engineered lipid remodeling system using a galactolipid synthase promoter during phosphate starvation enhances oil accumulation in plants", Frontiers in Plant Science, 6:664, 2015.

* cited by examiner

*Primary Examiner* — Matthew R Keogh
(74) *Attorney, Agent, or Firm* — Honigman Miller Schwartz and Cohn LLP; Fernando Alberdi; Jonathan P. O'Brien

(57) ABSTRACT

1) A fused gene including a nucleic acid sequence which affects the biosynthesis or accumulation of neutral lipid and a phosphorus deficiency-responsive expression control sequence which is operably linked to the nucleic acid sequence and controls the expression of the nucleic acid sequence, 2) a transgenic plant which contains the fused gene, 3) a method for manufacturing vegetable fat or oil, including a cultivation step of cultivating the transgenic plant, and 4) a method for manufacturing vegetable fat or oil in which the cultivation step is a step of cultivating the transgenic plant in a phosphorus-deficient state are provided.

14 Claims, 7 Drawing Sheets

Specification includes a Sequence Listing.

```
                          SEQUENCE LISTING

<160> NUMBER OF SEQ ID NOS: 30

<210> SEQ ID NO 1
<211> LENGTH: 520
<212> TYPE: PRT
<213> ORGANISM: Arabidopsis thaliana

<400> SEQUENCE: 1

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240
```

```
Leu Met Leu Leu Thr Cys Ile Val Trp Leu Lys Val Ser Tyr Ala
                245                 250                 255
His Thr Ser Tyr Asp Ile Arg Ser Leu Ala Asn Ala Ala Asp Lys Ala
            260                 265                 270
Asn Pro Glu Val Ser Tyr Tyr Val Ser Leu Lys Ser Leu Ala Tyr Phe
            275                 280                 285
Met Val Ala Pro Thr Leu Cys Tyr Gln Pro Ser Tyr Pro Arg Ser Ala
        290                 295                 300
Cys Ile Arg Lys Gly Trp Val Ala Arg Gln Phe Ala Lys Leu Val Ile
305                 310                 315                 320
Phe Thr Gly Phe Met Gly Phe Ile Ile Glu Gln Tyr Ile Asn Pro Ile
                325                 330                 335
Val Arg Asn Ser Lys His Pro Leu Lys Gly Asp Leu Leu Tyr Ala Ile
            340                 345                 350
Glu Arg Val Leu Lys Leu Ser Val Pro Asn Leu Tyr Val Trp Leu Cys
            355                 360                 365
Met Phe Tyr Cys Phe Phe His Leu Trp Leu Asn Ile Leu Ala Glu Leu
        370                 375                 380
Leu Cys Phe Gly Asp Arg Glu Phe Tyr Lys Asp Trp Trp Asn Ala Lys
385                 390                 395                 400
Ser Val Gly Asp Tyr Trp Arg Met Trp Asn Met Pro Val His Lys Trp
                405                 410                 415
Met Val Arg His Ile Tyr Phe Pro Cys Leu Arg Ser Lys Ile Pro Lys
            420                 425                 430
Thr Leu Ala Ile Ile Ile Ala Phe Leu Val Ser Ala Val Phe His Glu
            435                 440                 445
Leu Cys Ile Ala Val Pro Cys Arg Leu Phe Lys Leu Trp Ala Phe Leu
        450                 455                 460
Gly Ile Met Phe Gln Val Pro Leu Val Phe Ile Thr Asn Tyr Leu Gln
465                 470                 475                 480
Glu Arg Phe Gly Ser Thr Val Gly Asn Met Ile Phe Trp Phe Ile Phe
                485                 490                 495
Cys Ile Phe Gly Gln Pro Met Cys Val Leu Leu Tyr Tyr His Asp Leu
            500                 505                 510
Met Asn Arg Lys Gly Ser Met Ser
            515                 520

<210> SEQ ID NO 2
<211> LENGTH: 314
<212> TYPE: PRT
<213> ORGANISM: Arabidopsis thaliana

<400> SEQUENCE: 2

Met Gly Gly Ser Arg Glu Phe Arg Ala Glu Glu His Ser Asn Gln Phe
1               5                   10                  15
His Ser Ile Ile Ala Met Ala Ile Trp Leu Gly Ala Ile His Phe Asn
            20                  25                  30
Val Ala Leu Val Leu Cys Ser Leu Ile Phe Leu Pro Pro Ser Leu Ser
        35                  40                  45
Leu Met Val Leu Gly Leu Leu Ser Leu Phe Ile Phe Ile Pro Ile Asp
    50                  55                  60
His Arg Ser Lys Tyr Gly Arg Lys Leu Ala Arg Tyr Ile Cys Lys His
65                  70                  75                  80
Ala Cys Asn Tyr Phe Pro Val Ser Leu Tyr Val Glu Asp Tyr Glu Ala
                85                  90                  95
```

```
Phe Gln Pro Asn Arg Ala Tyr Val Phe Gly Tyr Glu Pro His Ser Val
                100                 105                 110

Leu Pro Ile Gly Val Val Ala Leu Cys Asp Leu Thr Gly Phe Met Pro
            115                 120                 125

Ile Pro Asn Ile Lys Val Leu Ala Ser Ser Ala Ile Phe Tyr Thr Pro
        130                 135                 140

Phe Leu Arg His Ile Trp Thr Trp Leu Gly Leu Thr Ala Ala Ser Arg
145                 150                 155                 160

Lys Asn Phe Thr Ser Leu Leu Asp Ser Gly Tyr Ser Cys Val Leu Val
                165                 170                 175

Pro Gly Gly Val Gln Glu Thr Phe His Met Gln His Asp Ala Glu Asn
            180                 185                 190

Val Phe Leu Ser Arg Arg Gly Phe Val Arg Ile Ala Met Glu Gln
        195                 200                 205

Gly Ser Pro Leu Val Pro Val Phe Cys Phe Gly Gln Ala Arg Val Tyr
        210                 215                 220

Lys Trp Trp Lys Pro Asp Cys Asp Leu Tyr Leu Lys Leu Ser Arg Ala
225                 230                 235                 240

Ile Arg Phe Thr Pro Ile Cys Phe Trp Gly Val Phe Gly Ser Pro Leu
                245                 250                 255

Pro Cys Arg Gln Pro Met His Val Val Val Gly Lys Pro Ile Glu Val
            260                 265                 270

Thr Lys Thr Leu Lys Pro Thr Asp Glu Glu Ile Ala Lys Phe His Gly
        275                 280                 285

Gln Tyr Val Glu Ala Leu Arg Asp Leu Phe Glu Arg His Lys Ser Arg
        290                 295                 300

Val Gly Tyr Asp Leu Glu Leu Lys Ile Leu
305                 310

<210> SEQ ID NO 3
<211> LENGTH: 285
<212> TYPE: PRT
<213> ORGANISM: Arabidopsis thaliana

<400> SEQUENCE: 3

Met Glu Lys Glu Lys Lys Ala Leu Lys Lys Lys Ala Lys Val Leu Lys
1               5                   10                  15

Ser Leu Ser Lys Asn Leu Asp Met Phe Ser Ser Ile Gly Phe Gly Leu
            20                  25                  30

Asp Pro Glu Ala Gly Leu Val Gly Glu Ile Gln Thr Lys Thr Ile Ser
        35                  40                  45

Glu Ala Thr Glu Ile Leu Val Lys Gln Leu Glu Gln Leu Lys Ala Glu
    50                  55                  60

Glu Lys Ile Leu Lys Lys Gln Arg Lys Glu Lys Ala Lys Ala Lys
65                  70                  75                  80

Ala Met Lys Lys Met Thr Glu Met Asp Ser Glu Ser Ser Ser Ser
                85                  90                  95

Glu Ser Ser Asp Ser Asp Cys Asp Lys Gly Lys Val Val Asp Met Ser
            100                 105                 110

Ser Leu Arg Asn Lys Ala Lys Pro Val Leu Glu Pro Leu Gln Pro Glu
        115                 120                 125

Ala Thr Val Ala Thr Leu Pro Arg Ile Gln Glu Asp Ala Ile Ser Cys
    130                 135                 140

Lys Asn Thr Ser Glu Ala Leu Gln Ile Ala Leu Gln Thr Ser Thr Ile
145                 150                 155                 160
```

```
Phe Pro Ser Met Ala Asn Pro Gly Gln Thr Leu Lys Thr Val Glu Ala
                165                 170                 175

Val Ser Val Val Gly Leu Pro Leu Asn Arg Val Glu Val Cys Met Gly
            180                 185                 190

Gly Lys Cys Lys Arg Ser Gly Gly Ala Leu Leu Leu Asp Glu Phe Gln
        195                 200                 205

Arg Ala Met Thr Gly Phe Glu Gly Ser Ala Val Ala Cys Lys Cys Met
    210                 215                 220

Gly Lys Cys Arg Asp Gly Pro Asn Val Arg Val Val Lys Glu Thr Asp
225                 230                 235                 240

Ala Val Met Thr Asp Ser Val Arg Thr Pro Ser Lys Thr Leu Cys Val
                245                 250                 255

Gly Val Gly Leu Gln Asp Val Glu Thr Ile Val Thr Ser Phe Phe Asp
            260                 265                 270

Glu Glu Cys Ser Arg Glu Gly Leu Gly Ser Val Ser Tyr
        275                 280                 285

<210> SEQ ID NO 4
<211> LENGTH: 701
<212> TYPE: PRT
<213> ORGANISM: Arabidopsis thaliana

<400> SEQUENCE: 4

Met Ala Val Thr Val Leu Pro Ser Val Ser Gly Leu Ser Ala Val Ala
1               5                   10                  15

Ser Ser Ser Asn Leu Arg Arg Leu Thr Ser Ala Ser Asn His Arg Leu
            20                  25                  30

Thr Ala Ile Lys Ser Val Thr Ser Thr Ser Pro Pro Thr Pro Ser
        35                  40                  45

Ser Gly Val Gln Arg Arg Arg Lys Asn Asn Asp Glu Asn Arg Ala Thr
    50                  55                  60

Val Ala Lys Val Val Glu Asn Pro Tyr Ser Lys Val Glu Ala Ala Arg
65                  70                  75                  80

Pro Asp Leu Gln Lys Arg Leu Ser Asp Phe Leu Glu Glu Ala Arg Glu
                85                  90                  95

Phe Val Gly Asp Gly Gly Pro Arg Trp Phe Ser Pro Leu Glu
            100                 105                 110

Cys Gly Ala Gln Ala Thr Asn Ser Pro Leu Leu Leu Tyr Leu Pro Gly
        115                 120                 125

Ile Asp Gly Thr Gly Leu Gly Leu Ile Arg His His Lys Lys Leu Gly
    130                 135                 140

Glu Ile Phe Asp Ile Trp Cys Leu His Ile Pro Val Ser Asp Arg Thr
145                 150                 155                 160

Pro Val Lys Asp Leu Val Lys Leu Ile Glu Glu Thr Val Lys Ser Glu
                165                 170                 175

Asn Phe Arg Leu Pro Asn Arg Pro Ile Tyr Leu Val Gly Glu Ser Ile
            180                 185                 190

Gly Ala Cys Leu Ala Leu Asp Val Ala Ala Arg Asn Pro Asn Ile Asp
        195                 200                 205

Leu Ser Leu Ile Leu Val Asn Pro Ala Thr His Val Asn Asn Phe Met
    210                 215                 220

Val Gln Pro Leu Ser Gly Met Leu Asn Val Leu Pro Asp Gly Leu Pro
225                 230                 235                 240

Thr Leu Leu Glu Asp Ile Phe Asp Phe Gly Phe Lys Gln Gly Asp Pro
```

```
                    245                 250                 255
Leu Thr Gly Met Leu Asp Ala Leu Ser Asn Glu Phe Ser Val Gln Arg
                260                 265                 270

Met Gly Gly Val Gly Gly Met Leu Arg Asp Val Leu Ala Val Ser
            275                 280                 285

Ala Asn Leu Pro Thr Leu Ser Arg Met Phe Pro Lys Asp Thr Leu Leu
    290                 295                 300

Trp Lys Leu Glu Met Leu Lys Tyr Ala Ile Ala Ser Val Asn Ser His
305                 310                 315                 320

Ile Tyr Ser Val Arg Ala Glu Thr Leu Ile Leu Leu Ser Gly Arg Asp
                325                 330                 335

His Trp Leu Leu Lys Glu Glu Asp Ile Asp Arg Tyr Ser Arg Thr Leu
                340                 345                 350

Pro Lys Cys Ile Val Arg Lys Leu Asp Asp Asn Gly Gln Phe Pro Leu
                355                 360                 365

Leu Glu Asp Gly Val Asp Leu Ala Thr Ile Ile Lys Cys Thr Cys Phe
    370                 375                 380

Tyr Arg Arg Gly Lys Ser His Asp His Ile Thr Asp Tyr Ile Met Pro
385                 390                 395                 400

Thr Thr Phe Glu Leu Lys Gln Gln Val Asp Asp His Arg Leu Leu Met
                405                 410                 415

Asp Gly Thr Ser Pro Val Met Leu Ser Thr Leu Glu Asp Gly Thr Val
                420                 425                 430

Val Arg Ser Leu Glu Gly Leu Pro Ser Glu Gly Pro Val Leu Tyr Val
                435                 440                 445

Gly Tyr His Met Ile Leu Gly Phe Glu Leu Ala Pro Met Val Ile Gln
            450                 455                 460

Leu Met Thr Glu Arg Asn Ile His Leu Arg Gly Leu Ala His Pro Met
465                 470                 475                 480

Leu Phe Lys Asn Leu Gln Asp Ser Leu Val Asp Thr Lys Met Phe Asp
                485                 490                 495

Lys Tyr Lys Ile Met Gly Gly Val Pro Val Ser His Phe Asn Ile Tyr
            500                 505                 510

Lys Leu Leu Arg Glu Lys Ala His Val Leu Leu Tyr Pro Gly Gly Val
            515                 520                 525

Arg Glu Ala Leu His Arg Lys Gly Glu Glu Tyr Lys Leu Phe Trp Pro
                530                 535                 540

Glu Arg Ser Glu Phe Val Arg Val Ala Ser Lys Phe Gly Ala Lys Ile
545                 550                 555                 560

Val Pro Phe Gly Val Val Gly Glu Asp Asp Ile Cys Glu Ile Val Leu
                565                 570                 575

Asp Ser Asn Asp Gln Arg Asn Ile Pro Ile Leu Lys Asp Leu Met Glu
            580                 585                 590

Lys Ala Thr Lys Asp Ala Gly Asn Ile Arg Glu Gly Asp Glu Ser Glu
            595                 600                 605

Leu Gly Asn Gln Glu Cys Tyr Phe Pro Gly Leu Val Pro Lys Ile Pro
    610                 615                 620

Gly Arg Phe Tyr Tyr Phe Gly Lys Pro Ile Glu Thr Ala Gly Lys
625                 630                 635                 640

Glu Lys Glu Leu Lys Asp Lys Glu Lys Ala Gln Glu Leu Tyr Leu Gln
                645                 650                 655

Val Lys Ser Glu Val Glu Gln Cys Ile Asp Tyr Leu Lys Val Lys Arg
                660                 665                 670
```

Glu Ser Asp Pro Tyr Arg His Leu Leu Pro Arg Met Leu Tyr Gln Ala
            675                 680                 685

Ser His Gly Trp Ser Ser Glu Ile Pro Thr Phe Asp Leu
    690                 695                 700

<210> SEQ ID NO 5
<211> LENGTH: 671
<212> TYPE: PRT
<213> ORGANISM: Arabidopsis thaliana

<400> SEQUENCE: 5

Met Pro Leu Ile His Arg Lys Lys Pro Thr Glu Lys Pro Ser Thr Pro
1               5                   10                  15

Pro Ser Glu Glu Val Val His Asp Glu Asp Ser Gln Lys Lys Pro His
            20                  25                  30

Glu Ser Ser Lys Ser His His Lys Lys Ser Asn Gly Gly Gly Lys Trp
        35                  40                  45

Ser Cys Ile Asp Ser Cys Cys Trp Phe Ile Gly Cys Val Cys Val Thr
    50                  55                  60

Trp Trp Phe Leu Leu Phe Leu Tyr Asn Ala Met Pro Ala Ser Phe Pro
65                  70                  75                  80

Gln Tyr Val Thr Glu Arg Ile Thr Gly Pro Leu Pro Asp Pro Pro Gly
                85                  90                  95

Val Lys Leu Lys Lys Glu Gly Leu Lys Ala Lys His Pro Val Val Phe
            100                 105                 110

Ile Pro Gly Ile Val Thr Gly Gly Leu Glu Leu Trp Glu Gly Lys Gln
        115                 120                 125

Cys Ala Asp Gly Leu Phe Arg Lys Arg Leu Trp Gly Gly Thr Phe Gly
    130                 135                 140

Glu Val Tyr Lys Arg Pro Leu Cys Trp Val Glu His Met Ser Leu Asp
145                 150                 155                 160

Asn Glu Thr Gly Leu Asp Pro Ala Gly Ile Arg Val Arg Ala Val Ser
                165                 170                 175

Gly Leu Val Ala Ala Asp Tyr Phe Ala Pro Gly Tyr Phe Val Trp Ala
            180                 185                 190

Val Leu Ile Ala Asn Leu Ala His Ile Gly Tyr Glu Glu Lys Asn Met
        195                 200                 205

Tyr Met Ala Ala Tyr Asp Trp Arg Leu Ser Phe Gln Asn Thr Glu Val
    210                 215                 220

Arg Asp Gln Thr Leu Ser Arg Met Lys Ser Asn Ile Glu Leu Met Val
225                 230                 235                 240

Ser Thr Asn Gly Gly Lys Lys Ala Val Ile Val Pro His Ser Met Gly
                245                 250                 255

Val Leu Tyr Phe Leu His Phe Met Lys Trp Val Glu Ala Pro Ala Pro
            260                 265                 270

Leu Gly Gly Gly Gly Pro Asp Trp Cys Ala Lys Tyr Ile Lys Ala
        275                 280                 285

Val Met Asn Ile Gly Gly Pro Phe Leu Gly Val Pro Lys Ala Val Ala
    290                 295                 300

Gly Leu Phe Ser Ala Glu Ala Lys Asp Val Ala Val Ala Arg Ala Ile
305                 310                 315                 320

Ala Pro Gly Phe Leu Asp Thr Asp Ile Phe Arg Leu Gln Thr Leu Gln
                325                 330                 335

His Val Met Arg Met Thr Arg Thr Trp Asp Ser Thr Met Ser Met Leu

Pro Lys Gly Gly Asp Thr Ile Trp Gly Gly Leu Asp Trp Ser Pro Glu
       355                 360                 365

Lys Gly His Thr Cys Cys Gly Lys Lys Gln Lys Asn Asn Glu Thr Cys
       370                 375                 380

Gly Glu Ala Gly Glu Asn Gly Val Ser Lys Ser Pro Val Asn Tyr
385                 390                 395                 400

Gly Arg Met Ile Ser Phe Gly Lys Glu Val Ala Glu Ala Ala Pro Ser
                   405                 410                 415

Glu Ile Asn Asn Ile Asp Phe Arg Gly Ala Val Lys Gly Gln Ser Ile
               420                 425                 430

Pro Asn His Thr Cys Arg Asp Val Trp Thr Glu Tyr His Asp Met Gly
           435                 440                 445

Ile Ala Gly Ile Lys Ala Ile Ala Glu Tyr Lys Val Tyr Thr Ala Gly
       450                 455                 460

Glu Ala Ile Asp Leu Leu His Tyr Val Ala Pro Lys Met Met Ala Arg
465                 470                 475                 480

Gly Ala Ala His Phe Ser Tyr Gly Ile Ala Asp Asp Leu Asp Asp Thr
                   485                 490                 495

Lys Tyr Gln Asp Pro Lys Tyr Trp Ser Asn Pro Leu Glu Thr Lys Leu
               500                 505                 510

Pro Asn Ala Pro Glu Met Glu Ile Tyr Ser Leu Tyr Gly Val Gly Ile
           515                 520                 525

Pro Thr Glu Arg Ala Tyr Val Tyr Lys Leu Asn Gln Ser Pro Asp Ser
       530                 535                 540

Cys Ile Pro Phe Gln Ile Phe Thr Ser Ala His Glu Glu Asp Glu Asp
545                 550                 555                 560

Ser Cys Leu Lys Ala Gly Val Tyr Asn Val Asp Gly Asp Glu Thr Val
                   565                 570                 575

Pro Val Leu Ser Ala Gly Tyr Met Cys Ala Lys Ala Trp Arg Gly Lys
               580                 585                 590

Thr Arg Phe Asn Pro Ser Gly Ile Lys Thr Tyr Ile Arg Glu Tyr Asn
           595                 600                 605

His Ser Pro Pro Ala Asn Leu Leu Glu Gly Arg Gly Thr Gln Ser Gly
       610                 615                 620

Ala His Val Asp Ile Met Gly Asn Phe Ala Leu Ile Glu Asp Ile Met
625                 630                 635                 640

Arg Val Ala Ala Gly Gly Asn Gly Ser Asp Ile Gly His Asp Gln Val
                   645                 650                 655

His Ser Gly Ile Phe Glu Trp Ser Glu Arg Ile Asp Leu Lys Leu
               660                 665                 670

<210> SEQ ID NO 6
<211> LENGTH: 1563
<212> TYPE: DNA
<213> ORGANISM: Arabidopsis thaliana

<400> SEQUENCE: 6
atggcgattt tggattctgc tggcgttact acggtgacgg agaacggtgg cggagagttc      60
gtcgatcttg ataggcttcg tcgacggaaa tcgagatcgg attcttctaa cggacttctt     120
ctctctggtt ccgataataa ttctccttcg gatgatgttg agctcccgc cgacgttagg      180 gatcggattg attccgttgt taacgatgac gctcagggaa cagccaattt ggccggagat     240
aataacggtg gtggcgataa taacggtggt ggaagaggcg gcggagaagg aagaggaaac     300

```
gccgatgcta cgtttacgta tcgaccgtcg gttccagctc atcggagggc gagagagagt      360
ccacttagct ccgacgcaat cttcaaacag agccatgccg gattattcaa cctctgtgta      420
gtagttctta ttgctgtaaa cagtagactc atcatcgaaa tcttatgaa gtatggttgg       480 ttgatcagaa cggatttctg gtttagttca agatcgctgc gagattggcc gcttttcatg      540
tgttgtatat ccctttcgat cttccttttg gctgcctta cggttgagaa attggtactt       600
cagaaataca tatcagaacc tgttgtcatc tttcttcata ttattatcac catgacagag      660
gttttgtatc cagtttacgt caccctaagg tgtgattctg cttttttatc aggtgtcact      720
ttgatgctcc tcacttgcat tgtgtggcta aagttggttt cttatgctca tactagctat      780
gacataagat ccctagccaa tgcagctgat aaggccaatc ctgaagtctc ctactacgtt      840
agcttgaaga gcttggcata tttcatggtc gctcccacat tgtgttatca gccaagttat      900
ccacgttctg catgtatacg aagggttgg gtggctcgtc aatttgcaaa actggtcata       960
ttcaccggat tcatgggatt tataatagaa caatatataa atcctattgt caggaactca     1020
aagcatcctt tgaaaggcga tcttctatat gctattgaaa gagtgttgaa gctttcagtt     1080
ccaaatttat atgtgtggct ctgcatgttc tactgcttct tccaccttg gttaaacata      1140 ttggcagagc ttctctgctt cggggatcgt gaattctaca aagattggtg gaatgcaaaa     1200
agtgtgggag attactggag aatgtggaat atgcctgttc ataaatggat ggttcgacat     1260
atatacttcc cgtgcttgcg cagcaagata ccaaagacac tcgccattat cattgctttc     1320
ctagtctctg cagtctttca tgagctatgc atcgcagttc cttgtcgtct cttcaagcta     1380
tgggcttttc ttgggattat gtttcaggtg cctttggtct tcatcacaaa ctatctacag     1440
gaaaggtttg gctcaacggt ggggaacatg atccttctggt tcatcttctg cattttcgga    1500
caaccgatgt gtgtgcttct ttattaccac gacctgatga accgaaaagg atcgatgtca    1560
tga                                                                   1563

<210> SEQ ID NO 7
<211> LENGTH: 945
<212> TYPE: DNA
<213> ORGANISM: Arabidopsis thaliana

<400> SEQUENCE: 7
atgggtggtt ccagagagtt ccgagctgag gaacattcaa atcaattcca ctctatcatc       60
gccatggcca tctggcttgg cgccattcac ttcaacgtcg ctcttgttct ctgttctctc      120
attttccttc ctccttctct atctctcatg gtccttgggct tgctctctct gtttatcttt     180
atcccaatcg atcatcgtag caaatatggt cgtaagctcg ctaggtacat atgcaagcac      240
gcgtgtaatt atttccccgt ctctctgtac gtcgaggatt acgaagcttt ccagcctaat      300
cgtgcctatg tctttggtta tgaaccacat tcggtgctac cgattggagt tgttgctctt      360
tgtgatctca cagggtttat gcctattcct aacattaaag ttcttgcaag tagtgctata      420
ttctacactc ccttttctaag gcatatatgg acatggttag ggctcaccgc tgcttctagg     480
aagaatttca cttcccttttt ggattctggc tacagttgtg ttcttgtacc tggtggtgtg     540
caggagactt tcatatgca acatgatgct gagaatgtct tcctttcaag gagaagagga       600
tttgtgcgca tagccatgga acaggggagc cctctggttc cagtattctg ctttggtcag      660
gcacgcgtgt acaaatggtg gaagcccgat tgtgatctct atcttaaact atctagagca      720
atcagattca ccccgatctg cttctgggga gtttttggat caccattacc gtgtcgacag      780
```

| cctatgcatg tggtcgttgg taaaccaata gaagtcacaa aaactctgaa gccaactgac | 840 |
| gaagagattg ctaagtttca tggccagtat gtggaagcgc ttagggatct gttgagagg | 900 |
| cacaagtccc gagtcggcta tgatcttgag ctgaaaattc tttga | 945 |

<210> SEQ ID NO 8
<211> LENGTH: 858
<212> TYPE: DNA
<213> ORGANISM: Arabidopsis thaliana

<400> SEQUENCE: 8

| atggagaagg agaagaaggc gttgaagaag aaggcgaaag ttcttaaaag tctttctaag | 60 |
| aacttggata tgttctctag tatagggttt ggtcttgatc ctgaagctgg tttggttggt | 120 |
| gagattcaga ccaagacaat ctcggaagct acagagatat tggttaagca gctggagcag | 180 |
| ttgaaagcag aggagaagat attgaagaaa cagaggaaag aagagaaggc taaagccaaa | 240 |
| gccatgaaga gatgactga atggactct gaatcatctt cttcgtctga atcaagtgat | 300 |
| agtgattgtg ataaaggcaa agttgtggac atgagctctt taagaaacaa ggctaaaccg | 360 |
| gttcttgagc cgttacaacc agaagccaca gtagcaaccc ttcctaggat ccaagaggat | 420 |
| gcaatttctt gcaagaacac cagtgaagca ttgcagattg ctctacaaac atccacaatt | 480 |
| tttccttcaa tggccaatcc tggacagaca ttgaagacgg tagaagcggt ttcagtggtt | 540 |
| ggattaccat tgaatagagt agaagtgtgt atggagggga agtgtaagag atcaggagga | 600 |
| gctttgttgt tggatgagtt caaagggcg atgacgggtt cgaaggatc tgctgtggct | 660 |
| tgcaagtgca tggggaagtg tcgtgatggc ccaaacgtta gagttgtgaa ggagactgat | 720 |
| gctgtgatga ctgattcagt taggacacca tccaagaccc tttgtgtagg agttggattg | 780 |
| caggatgtgg aaactattgt gacaagtttc tttgatgaag aatgtagcag agaaggactc | 840 |
| ggttctgtct catattga | 858 |

<210> SEQ ID NO 9
<211> LENGTH: 2106
<212> TYPE: DNA
<213> ORGANISM: Arabidopsis thaliana

<400> SEQUENCE: 9

| atggctgtta cagtacttcc ttccgtctcc ggtctctctg ccgtcgcatc ttcatcgaac | 60 |
| ctacgacgtc tgacctccgc ctcgaaccat cgactcacgg cgataaaatc cgtaacatct | 120 |
| acttcttctc ctcctacccc ttctagtggt gttcaacgga gacggaagaa taatgatgaa | 180 |
| aacagagcca cggtggcgaa ggtggtggag atccgtatt cgaaagtgga ggcggcgcgt | 240 |
| ccggatttgc aaaagaggtt gtcagatttt ttggaagaag ctagagagtt cgtcggagat | 300 |
| ggaggaggtc cacctcgttg gttctctcca ttggagtgtg gcgctcaagc tacaaactct | 360 |
| cctcttctcc tatacttacc tgggattgat ggaactggac taggtcttat tcgccatcac | 420 |
| aagaaacttg gggagatttt tgatatatgg tgcctgcaca taccagtcag tgatcgtact | 480 |
| cctgttaaag acttggtgaa gcttattgag gaaaccgtta agtcagagaa ctttcgttta | 540 |
| ccaaatagac caatatattt agttggagaa tctattggag catgtcttgc tttagatgtt | 600 |
| gcagccagaa atcccaacat cgatctttct ctgatcttgg ttaatccagc cacacatgtc | 660 |
| aacaacttca tggtgcaacc tctatcagga atgctaaatg ttttacccga tggtcttcca | 720 |
| acgctattgg aagatatctt tgattttggt tttaagcaag gcgatccatt aactgggatg | 780 |
| ttagacgctt tgtcgaatga attttctgtc cagcgaatgg gcggagtagg tggagggatg | 840 |

```
ctaagagatg tccttgctgt ttcagctaat cttcctactc ttagtaggat gttccctaag    900
gacacactgc tttggaagct ggaaatgctt aagtatgcta ttgcttctgt gaactctcac    960
atatactcag tcagagcgga aacactcata cttctgagtg gacgcgatca ttggctcctg   1020
aaggaggaag acattgacag atactcgcgc acgttgccaa aatgtattgt ccgtaagctc   1080
gacgacaatg gacagtttcc ccttttggag gatggtgtag atcttgctac tatcatcaag   1140
tgtacttgtt tttatcgccg tgggaagtct cacgatcaca ttacggatta cattatgcct   1200
accacatttg agttaaaaca acaagtagac gatcaccgat tgctaatgga tggtacttct   1260
cctgtaatgc tgtcaactct agaagacggc acagttgtaa ggagcctcga aggattacct   1320
tcagagggac ctgttttgta cgttggctat cacatgatat tgggatttga gttagctcca   1380
atggtaattc aactcatgac agagaggaac attcacctgc ggggtttggc acatcccatg   1440
ctatttaaga atctccaaga ctcattagtc gacacgaaga tgtttgacaa atataagata   1500
atgggtggag ttccagtctc ccatttcaat atctacaaac tactgcgtga aaaggctcat   1560
gtgcttctgt atcctggagg tgtccgtgaa gctttgcata gaaaaggtga agaatacaag   1620
ctgttttggc cagaacggtc cgagtttgtg agagttgcat ctaaatttgg agccaaaatt   1680
gttccttttg gtgttgttgg agaagacgat atctgcgaaa ttgtcctgga ttctaatgat   1740
caaaggaaca tccctatcct caaggattta atggaaaagg caacaaagga cgctggcaac   1800
ataagggaag gcgatgagag cgaattggga aaccaagagt gctatttccc aggacttgta   1860
cctaagattc cagggcggtt ctactattac tttggcaaac caatagaaac agcaggtaag   1920
gagaaagaac taaaagacaa agagaaggca caagagctct acttgcaagt taaatctgag   1980
gtagaacaat gcattgacta tttaaaagtg aaaagagaga gtgatcccta cagacactta   2040
ttgcctagga tgttgtatca ggcctcacat ggttggtctt ctgaaattcc aacgtttgat   2100
ctctaa                                                              2106
```

<210> SEQ ID NO 10
<211> LENGTH: 2016
<212> TYPE: DNA
<213> ORGANISM: Arabidopsis thaliana

<400> SEQUENCE: 10

```
atgccccttta ttcatcggaa aaagccgacg gagaaaccat cgacgccgcc atctgaagag     60
gtggtgcacg atgaggattc gcaaaagaaa ccacacgaat cttccaaatc ccaccataag    120
aaatcgaacg gaggagggaa gtggtcgtgc atcgattctt gttgttggtt cattgggtgt    180
gtgtgtgtaa cctggtggtt tcttctcttc ctttacaacg caatgcctgc gagcttccct    240
cagtatgtaa cggagcgaat cacgggtcct ttgcctgacc cgcccggtgt taagctcaaa    300
aaagaaggtc ttaaggcgaa acatcctgtt gtcttcattc ctgggattgt caccggtggg    360
ctcgagcttt ggaaggcaa acaatgcgct gatggtttat ttagaaaacg tttgtgggt     420 ggaacttttg gtgaagtcta caaaaggcct ctatgttggg tggaacacat gtcacttgac    480
aatgaaactg ggttggatcc agctggtatt agagttcgag ctgtatcagg actcgtggct    540
gctgactact ttgctcctgg ctactttgtc tgggcagtgc tgattgctaa ccttgcacat    600
attggatatg aagagaaaaa tatgtacatg gctgcatatg actggcggct ttcgtttcag    660
aacacagagg tacgtgatca gactcttagc cgtatgaaaa gtaatataga gttgatggtt    720
tctaccaacg gtggaaaaaa agcagttata gttccgcatt ccatgggggt cttgtatttt    780
```

```
ctacatttta tgaagtgggt tgaggcacca gctcctctgg gtggcggggg tgggccagat      840
tggtgtgcaa agtatattaa ggcggtgatg aacattggtg gaccatttct tggtgttcca      900
aaagctgttg cagggctttt ctctgctgaa gcaaaggatg ttgcagttgc cagagcgatt      960
gccccaggat tcttagacac cgatatattt agacttcaga ccttgcagca tgtaatgaga     1020
atgacacgca catgggactc aacaatgtct atgttaccga agggaggtga cacgatatgg     1080
ggcgggcttg attggtcacc ggagaaaggc cacacctgtt gtgggaaaaa gcaaaagaac     1140
aacgaaactt gtggtgaagc aggtgaaaac ggagtttcca agaaaagtcc tgttaactat     1200
ggaaggatga tatctttggg gaaagaagta gcagaggctg cgccatctga gattaataat     1260
attgattttc gaggtgctgt caaaggtcag agtatcccaa atcacacctg tcgtgacgtg     1320
tggacagagt accatgacat gggaattgct gggatcaaag ctatcgctga gtataaggtc     1380
tacactgctg gtgaagctat agatctacta cattatgttg ctcctaagat gatggcgcgt     1440
ggtgccgctc atttctctta tggaattgct gatgatttgg atgacaccaa gtatcaagat     1500
cccaaatact ggtcaaatcc gttagagaca aaattaccga atgctcctga gatggaaatc     1560
tactcattat acggagtggg gataccaacg gaacgagcat acgtatacaa gcttaaccag     1620
tctcccgaca gttgcatccc ctttcagata ttcacttctg ctcacgagga ggacgaagat     1680
agctgtctga aagcaggagt ttacaatgtg gatgggatg aaacagtacc cgtcctaagt     1740
gccgggtaca tgtgtgcaaa agcgtggcgt ggcaagacaa gattcaaccc ttccggaatc     1800
aagacttata aagagaata caatcactct ccgccggcta acctgttgga agggcgcggg     1860
acgcagagtg gtgccatgt tgatatcatg ggaaactttg ctttgatcga agatatcatg     1920
agggttgccg ccggaggtaa cgggtctgat ataggacatg accaggtcca ctctggcata     1980
tttgaatggt cggagcgtat tgacctgaag ctgtga                               2016

<210> SEQ ID NO 11
<211> LENGTH: 2000
<212> TYPE: DNA
<213> ORGANISM: Arabidopsis thaliana

<400> SEQUENCE: 11
tagtcttaga aaatgccaaa gcaacgacaa agtcaagatc gtcgttggtc tataagaagc       60
aaaaacgctc aacaaattca agatcctcta aactcaagta gaaacaatgg agaagccaaa      120
gttcaagact gtccaagagg tggttgcagc tggcgaagga ctgccggaga gatatctcca      180
cgcacccacc ggagacggcg aagttcaacc tcttaacgca gcggtaccgg agatggatat      240
tccggccatc gatctgaatc ttctcctctc ttcttctgaa gctggtcaac aagagctgag      300
taaacttcac tcggcactct ctacatgggg cgttgttcag gtttgaccct cttagtgatt      360
gatcagagta atgaaatctt gtagaagttc cggtgaggag gtgatatcat ggaagttggt      420
ttcttatcga tgcaggtgat gaatcatgga attacaaaag cgtttcttga caagatttac      480
aagctaacca aggagttctt tgcgcttccg accgaagaga aacagaagtg cgcgagagag      540
attgatagta tccaaggata tggtaacgac atgattcttt gggatgatca agttcttgat      600
tggatcgacc gtttgtatat tactacttac cctgaagatc aaagacaact taatttctgg      660
cctgaagtcc cacttggatt caggtaaagt ttattatacc ttttcagttt aaacagcatc      720
tttgttcatt gagtttggtg attttgacat attgtttgtt tagggaaact ttacatgaat      780
acacaatgaa gcaacggata gtgattgagc aattttttaa ggccatggct agatctttgg      840
aattagaaga gaatagtttt ctagacatgt atggagaaag tgctacgttg atactagat       900
```

```
tcaacatgta tccaccatgt ccgagcccgg acaaggttat tggtgttaaa ccgcacgctg      960
atggctcggc tatcactctt ctcttacccg acaaagatgt cggagggctt cagttccaga     1020
aagatgggaa gtggtataaa gctcctatag tccctgatac aattttgatc aatgttggtg     1080
atcaaatgga ggtaatcagt cacctacata tatgaatatg attttgaaag attaattgat     1140
gtagatttga cataaataaa tctctatttc tcgtgtgttt tcagataatg agcaatggga     1200
tatacaagag cccggttcat agagtggtga ctaacagaga aaaggaaaga atatctgtgg     1260 caacttttg cattccaggt gcagataaag agattcagcc tgtgaatgag cttgtgtctg      1320
aggcaagacc aagattatat aaaacagtta agaagtatgt ggagctctac ttcaagtact     1380
atcaacaagg ccgaagacct attgaagctg cattgatctg atcacacttt tcaagtctca     1440
tttattggtt tcacaaatga atctgtttct ttcgttactt gagatccttt ataagaataa     1500
aactgtttcc ttgtttgttg aatgtgaggc tgcattgtg ttgcaattct gagaccagaa      1560
atataagtct aaagttgatt tccatattca gttctaacac taaaaacaga ggttaaccca     1620
aaaacagagc tcaacactaa aacagataag taaaattatt tttgcatagt tgttatatac     1680
tactgaatat tcttttgtta ataattctag gtttatatta cttttcgagg accttgaata     1740
ttcgaatctt ttcaaatcga acattccaaa ataagtcac gattcttacg gctgtcatca      1800 tggacaacc agtcttctct gttttttcttc catgattctc tcttacaaca tcaatcgttc     1860
acccaaacac cctttctttc tctgtctctt tcctcggaaa tttctccttc tccggtgtcg     1920
aatcgccgag ggaaggtgat ttttccggga aagtctccgt tttgtttcac ctaatcatct     1980
caaagactcg tcctttataa                                                 2000

<210> SEQ ID NO 12
<211> LENGTH: 2000
<212> TYPE: DNA
<213> ORGANISM: Arabidopsis thaliana

<400> SEQUENCE: 12
atggaagccc ctgaaccgac ttttttaata agtcctttac aaaccagaga tctaactgaa       60
caaatacttc tccagccata agacggagag tatgatttta tattttccag aggattggat      120
ttcctaaaat atcttcgttt aaaaaccttg gcaaagagag agtccggaaa cgaaactaga      180
cgccataact gtttcgctaa taatgcagag tttaaatcat ctacatcccg aaaaacctttag    240 tcacttccca atttactagt acacagtttg ttccaagtca tccagtgtat acctctagat      300
tcaccattcg agctccacca aaatcctgcg accgcacttg ttagtttgga agtaattgtt      360
ttcgggagcc taaagcaata catcacataa gttggtaatg ttgcggctac tgatttaatc      420 atcactttt tccctccttt tgataggaat ttagttgacc acccatttat tcgactgtaa       480
tcgatcttta acaacggaaa agatctttgt cttagatccc cctaaactct caggtagtcc     540
gagataggaa cccatgcctc cgatattatg tatacccaag atcgatttta tttctgcctt     600
tatagcttca tctactttat gcccgaactg aatcgatgat tttacaaaat ttatcatatg     660
tcctgatacc gcttcatatt gttttagaat acccaatagt taatagactt attatacccca    720 cattagtctt aatttctttg aatgtcacta tatttatttt ttaaatttat atttgtaatt     780
atgtttatcg cacataaatt tttcatatag tattaagttt tcttgatttt actacttcta     840
aaaaaataaa atgagatttt caattatat tataccaaat aaattaaatt gtgaaaattg      900
aaccacagat ttaaaacata atgtacaact atttcatata aacaacatt cttttctttta     960
```

| | |
|---|---|
| ggatagttac agtaatatac caaaaatcaa atttaaaata aattaaaatt ttaataatgt | 1020 |
| tctgtaataa agagaaaaat atataataaa acacgtacta atgcatcata aaatacacat | 1080 |
| tttatgtact aataagtata ataaacatgt tatcttaact aaacataacc aagtaaaaaa | 1140 |
| aacatactac tatatcaata aaagtaaata catataccaa gtaagttgaa aaaataaaac | 1200 |
| tattgctcag ttatttatat atagattata ttaaattgaa acaacaatta actttctaac | 1260 |
| gcaaataatc aactcgctgt gtaccgcggg tcaatatcta atgatgtcat aattctcgta | 1320 |
| gacaaataga caatttttcc atatgagtac atttgatgca aaagtagaca tttgaactga | 1380 |
| aacctatttt tgtttacaaa cattcatatc aacaactaaa caaaaatcga aactaacttg | 1440 |
| aatcaattaa tcaagtatta aattaatatg aaaagtggac tcaaatttaa ctgaatcgat | 1500 |
| ttaaacctaa tcaaaccaga taattttttga ttctaaaccg gtttacctat gtcacaaaaa | 1560 |
| ggaccatcca tgtcatattt ttttttttaat tttaaaaag tcaagttgtt ttaaatatac | 1620 |
| ttgagatgca aagaaagatc cgaatcatat atccgaagat tccgaaacca aaggcggatc | 1680 |
| cgacggctcc aagctgccat attcccttgt tactctacca ctaaattaag ccccacataa | 1740 |
| aacaataaag acacgaaata taaataccta agcaaaacta taggaaccga aaaaaaaaa | 1800 |
| aaagaataat tccagcatca ttcctcaagt aatttaaaaa caattattaa aagaagcaac | 1860 |
| ttggtcttcc atttttttttg ctacaaaaaa tttaaaaccc caaaagaact taaaatcttt | 1920 |
| tacataaaga tcaccaacca gccacataga aaacacaacc atcggtcttc ttattattct | 1980 |
| ttcttcaaca ccaaatagtc | 2000 |

<210> SEQ ID NO 13
<211> LENGTH: 2000
<212> TYPE: DNA
<213> ORGANISM: Arabidopsis thaliana

<400> SEQUENCE: 13

| | |
|---|---|
| ttagttttgg taatcttatt ataacaatca gaatcattgt aaaccatttg agaaacagag | 60 |
| caatcaaaga gttttgaatt taccgcccaa atattcttac gtattttttt tacttataat | 120 |
| taatctacat gttcttttttc ttttctagtg atgccacttc ctagaaaata ccagttatgg | 180 |
| taagtttagc tatatgtcac cacaatgaca ccatgcaatt ttacgacatc catattaatt | 240 |
| gttaagctta atatatatac aaaacgatga tatttgcaag ggatttggtg accaatagat | 300 |
| gcactctaat tatacacgag atcctaaaat tgcaagatac gagagaggga aataagtcaa | 360 |
| gtatgagatt aatctatgcg cctaaaacaa gttttttttat tgcatgggat ccagggccgg | 420 |
| cctcatgaca tgatcgatca catcagcctg agatcgctga tgtttacttg atcaataaaa | 480 |
| gacggctatt gttatattc cgaattttca tatgcattga taaagattat taacgtaaaa | 540 |
| catatatgca tatttttaaac tttgtgtggt ttgtttagtt ttaatataca tttttttgct | 600 |
| aatatccaag gctagagcac tgaattcttt ctacatgtga atattgtgtc ggtaagcctt | 660 |
| ttgaataatt cacaatcctt agaagatttc ctcaaaaaca atgttcaatt ttgagagaat | 720 |
| ataatgaatt ttcaatttta caaaaattaa cttgaaagat cttttttttcct tcttcctaat | 780 |
| ttataattcg taaataatta catcattttt tgtgctttct tctgctcgat gaatagatga | 840 |
| ctaataaatg ttagagagca aagctgaata ggagaattat gtacatctta tgtgcatctt | 900 |
| aattttaaac atggtgttgt gttggaaaac attagagaca tcgttacgtt gattatgtag | 960 |
| atatttgtta tgaatgctct tctaagtggt tgtgtaatgt atataaatta tcacatccac | 1020 |
| ctacctccta ggaacctttt tgacgtggaa cttgaagatc ctagtttgaa gaattttgag | 1080 |

```
tttctactgc cgacacaaag ataaattagc cattgtcgaa gtcgcagaaa agaccataga    1140
aaaggctgtt agggatatgc aacctcattt actgcagatt atagtccaat ggtatatgag    1200
aggtatcata gagtcttgtg aagaagatga agaagatttt agttgaggga tgttctgtct    1260 gattttatt gcattttgga tatagataat caaccgattg atctcttgtt gttaaccaag    1320
gtcttttcct tcataaatgt tttggcccat gttcttctag tctatgtttg tgggagtggg    1380
atgggatggg taatatacgt tgctattaga gtcctcaat tatgctctga gaatcgaaaa    1440
ggtattttca ttgtcatcca aaatcataaa ttcatatttt gctgcttcat taaactgtgt    1500
cctgaaaaat acatctatgc aatttattct cttatacaga caatgcagaa atatggtgaa    1560
tttccattag actataaagg taatattact tctgcttcta cttagaaaag cacagcaaaa    1620
ttggtaccat agtccaaaat gtgtgaaata gttttcagta aaatgtattt atagtaattt    1680
ttggggtaaa atgttaagta ttttataggg atttgatgag gtattcttca attgtccaga    1740
tttgtataga ctcaaaatgt gagagaacga aaaatatcca taactaataa gcatatgatg    1800
cttataattt tgatttactt ctaactttaa atggggcact ttacttgacg tgataccaat    1860
tcaaaggaca ataagcatgc atgatgcgta tttcttattt gcttttact tgtaaatatc    1920 tatctcttca atttgtcaag cactataaac ccacgatctt ctcaaacttt catcaataat    1980
tcaattggaa aacaaataga                                                2000

<210> SEQ ID NO 14
<211> LENGTH: 2000
<212> TYPE: DNA
<213> ORGANISM: Arabidopsis thaliana

<400> SEQUENCE: 14
tctttgtagg ttggtagaga ttctcggcct gtgatgcgag aagcttataa tctattcaag     60
aatggtggtg atcctgaaaa ggttttgaga catgtttctt gataattgat atcattgatt    120
tatttccatc aaacgatctt aatactctga ttttgaaata cagttagtaa atgacttctc    180
tagcggtcaa gcaagcgaat acttctatgc ttctctgtac gcagggctct actatgaagc    240
tgaggtaagc tcttgatctt gaatttatcc aagacaatct ccattgacat ctattggcct    300
attgctattc aaaaacaaac aatccttgag taatcttgtt taagttactt gtctgattct    360
tgttgtaggg taaatcagaa aacgcaaagt ttcatttaac cgcggcttgt ggatctccat    420
atgggcagag gtttgaaccc ctatagcata ttggtagcag ttataaagtg attcgatggt    480
ctagtgtttt tgatactttt catcccaaat ttgtttcagg tctgatgatt atatggcttc    540
acttgctaaa gtccattgcc tttgtagaaa ctggagctcc ggtattcttt gaaccggttc    600
atggttttgt ggagccaaca tattagttat taaggcccaa ttttgaaat atcagcccaa    660 ttaaaaattg gacctgggtt tgcgatttcc aacctttatt tatgggcatg aataaagaaa    720
gtaccattca caaacattat aacaaatagg caacattgtg ccattttgga gtaccattca    780
caaacatttt aaccaaatta ttgtagaaat tttcgtacca agtatcttaa tctggataat    840
aatttcactg aacgttctgt ttaatataca ttagttttat actggttgat cgtttgatac    900
taatatctat gaacttaaat ataatttaat tgtatttgcg aattgcttta gatgaacaac    960 aactttacg agatccaaaa attgttattc cgttttttg atggaaaggt agtatatatg    1020
ttgtgtagac agattagttt agtaactatg ttgaataagc tatatttaa ttgtccggac    1080 tgtactttat atctgtaaaa taaatagttg aaagaaaatc atattgacta gtatttttg    1140
```

```
ttatggttta cttaagggat gaagaaaagt ggagatggag actcaaatca ttttttttc    1200
tcatcacaca tgttgtaaga attaaataag tgtgtttggg aatattctga tctggcaaag    1260
caccaaaaaa ttgggatatt cttgtcgtct gatgcttgca tggcatatac ttcgtacatc    1320
agcaactcct gcatcagcaa aatacaaaat tatccctcca tagtccatac taacagaacc    1380
ggaaattacc ggcgaatgtt cggtacatga catttctaaa gtttattcaa ttttttttct    1440
tagtttattc aatcttaaca tctattaaat aatttaaaat gaaattcatg ccaacgcgaa    1500
aatgattttc ttatttattg aaacatcgtt tttaatccat ttttctgaaa accgatacga    1560
aaaagagaaa aaagttattt ttagcaagga aaagtttaag ggtaaaatcg tcatttggct    1620
acttagtctg ggacagttaa aaaattaaac aatccagagc tcttgtccaa tttggagacg    1680
atgtaaccaa gttgcatata cacggcaggg tagacgggag ttaatacata ccctcgatct    1740
taaacgtaca cgtgacaata atcgtacgtg tcatcatctc gaaacgcaac ccggtcattc    1800
gttaaaccta acgtgacgga accactccct ttgccgttga atgtactatt tgacagactg    1860
atttaaacct tatattctaa ataaaatcta aaatcaatag acacctatat aacgtcgatt    1920
tattgatcag tggaatctcg agtatttcgg acatgcaatc gtgaacggcg agtttcgacg    1980
acggtttggg gagttaatcg                                                2000

<210> SEQ ID NO 15
<211> LENGTH: 2000
<212> TYPE: DNA
<213> ORGANISM: Arabidopsis thaliana

<400> SEQUENCE: 15
atggccggac tgagtgaatc cgaacttttc gaagagaatc atcggcctag aatcgtcgga      60
gattgtgaga gatttgatct ccgccgccgt gcgagtgatg caacttgcgg agaagaggag     120
gaggacgacg aagagggggta gtctcgtcat attcgcgccg taactgtaga ggtgagaaac     180
aacgatgctt ctcgtgattt ctggtttcgt tttaagctta agcttgaagg aagaaacgag     240
aatggcgttt tgaccagatt taatgctgag gaaacgaaac gacgccgtct ctcatacgga     300
aaattctggc agcccgtaat ggttgatttg actcgaattt aaacaaagcc cattgggcct     360
aatttgatag agttggaagt caaaacttaa tatgaaagag aacggtttgg taacagtaca     420
tggtaagaga atgtgtaaca cgtgcggtgt cacctgtctt cttctctcac atatctgtag     480
ccatttaata ttccgcttaa gagaaaacaa aaacctgttc atatattaaa atatgactgt     540
gctgttatat tttatatgc gaaaaagggc ttagcgtatt aaatttatcg gagcgaccaa     600
cgtgaatcgg taacattaat ggaaatgat ttgacttaga agaaaacgag ttaggtgaga     660
acgtagcaac ataggacact tgtgaacgat gcttatttc aaatttttac attttatāa     720
agagattgaa cacaataaat tggctaacta aataaacaaa ttgattttgc gtatagacaa     780
agaatatacc agatatgcta ttgtgtggat cactaatatt cccacgagtc cacgactatc     840
ccatttctt tttctctatt ttatgaacat ttatttaata gattaatttc acttatgtct     900
ttaccaagac tatattcaa tttttatäa aactatttc tcatttatca tcaagaagtg     960
aaaaaaataa tagatttaaa cgttgtttta aaaagtagat ttaaacaaaa aaaggtgga    1020
aacttaatttt ttgtggtcaa aaatatatta attcagcata tttgtttct tttgtgtaaa    1080
atcaagcata ttcttttcgca ggttttaata tggaaatacc aaaagtaccc tcttagagaa    1140
gcaataatta cgacaaaagt cgaagagaga cccttctcgt aattctccct cctcccttca    1200
cagagtcatc tcatcatctt atataagcaa ttacagtctc ttaagttcat ggcggattta    1260
```

```
atttgttctg gttatccaaa acaaccatct ttttcctctt tcttataaat ctctcccacc    1320
ggtagcggta aaatacaatc gtcgaagcaa agacaaatcc ttttgactt tcattaaaaa    1380 ttccgagaat cttttatca acccaatatt tttttttat cccccgagag agaaatttca    1440
atgaaattct tagtatagga tacaattcat taaaatccat ttcattttca atagtaatct    1500
cgattactga ttcgtcgttt cttccgccgt gttttgattt ttctcggatt ctccgctcag    1560
agttcctaat ctgtgtaagt tgatttcgat tttccgactc tgagattttt aaatgtttgg    1620
ttcgtgggct atcatcgtat ctcgttgtat cttcccaaca atttgaaagc tgtttgattt    1680
ttcttctttg ggttgtgtta gttcagaaac tgttaaagtt gcatgcttga aattgggaaa    1740
atggttggat acttgtgtaa tcggaacatt acgaatggtt tttttttgta tctgattgat    1800
ttgattttcc tccttatgag ttttttgttt ttagtctctc acatgttatt gttctctaat    1860
tttggcttgt tgttgggttg ttttgtttca cctgtaggct ggaattaacc tgtctaagaa    1920
actaaacttt ctctagtttc tagatttttg tatatgatta ggacagtaaa agttgaagac    1980
tttctcaaag atttgatgaa                                                2000

<210> SEQ ID NO 16
<211> LENGTH: 2000
<212> TYPE: DNA
<213> ORGANISM: Arabidopsis thaliana

<400> SEQUENCE: 16
attctggaaa agggaacatt ttccatggaa actccggcag acatgggtcg gacaaagctt      60
tggatccgcc cgagagcatg tgaacgaacc ctgttgcgag gataactcct gctgcgaacg     120
ctttggctcc cctcattaag ccaccgttta acggaagtag ggttccaact agaggaatcg     180
agactccggc agctccggag ataaggatcg acgccatagc tgcgaacttg agggtaagag     240
cagctgcgtc atctcggcac gggtctgagt cgcccgagtc acagctagtt gtgaacgact     300
ctgttttgtt acatgcaaaa ataaattgag ttaactttgc taagaaaatc tcaaaatttg     360
catttaagtg tgtttaagag cgaaatgaag taattgcttt gagatttgaa gtgacaatac     420
ctgtcaaacc agatgataat ggtcgaagaa actgccaaaa atcctgaaaa cattatgagg     480
caaaattatg tgaggaaaca ggattgaaga agcaaaataa cattaaatag atgaagtgga     540
agaagtttca gacctgtaag agagacattt actaaatccg attaggcgat taaacttgta     600
gaattatata aattattgcc aaggaaacca gcaagctaag tatatatggg ttattaatat     660
tatggagttg tctgtgtgtt ttataaagaa agattgggaa aatgtcaatc agtgcgaggg     720
tttgtgtgtg cgtgcacgta cgttaacaag gtcacatgag gttcacggga atcaaatgac     780
catagaatgt cgtcattttc atctagtacc ctcattgaca agaatattaa agtttggaag     840
ataataacta cgagaaaaca aatatagaat tagagatgag atgtatgaga atgttttgtt     900
ataattgaag tctttgttcg tatcttgcat cagaagtatg actcttgttt ggtcaacttg     960
cagaaaaatg actattacaa tgcgaaatac tagtaatgtt ttgcgtctta ataaaatttc    1020
attcaaaaga ttatgtaagt taggtttgca ttttacagtt gattttgttt ttctcctatc    1080
tcatgattct ctgttttaat aattaaaagt taaaatttag aaaatagcca caaacatatt    1140
caaaaagtat atatttgggc caaccggccc agtaagggaa gaatgttcct taagttgcct    1200
aaatgagcga ctgagaaact ggcccacaaa ggccggacct gtatcattca caaccggaaa    1260
actttaaaac taataaaacca acgttcttaa aaaagcgaca ctttgggcca taatttgttg    1320
```

| | | | | |
|---|---|---|---|---|
| ggaagggaat | aagtaagaat | atgctttggg | catatctgat | gatttatatc | tgtctcatct | 1380 |
| catctctcat | cgttccggga | gaagagaaga | gagacccatc | cctcacttca | aagttcaaag | 1440 |
| tctcgaagga | tcttctccaa | ctctctctaa | acaagattcc | aaattttcaa | aggtaagcaa | 1500 |
| tcgtttcttc | taatgaattt | catttctccg | gttttgtaag | ttgagtgatt | tcgttttgaa | 1560 |
| gaaactctga | atatgatagg | aaatcaaaat | tcacagagtt | ttcattcagt | tgggttttct | 1620 |
| ctgaatttca | tcaatgtact | tctttcttac | atttactta | gttgatcaaa | taaatatcca | 1680 |
| gtctttgaca | atagctgatt | ttcagattcg | ataaaagact | tcaaatttcg | tgtgttttga | 1740 |
| ttcttctctt | gttatggacg | tagctgattt | agggggggg | gtgtgaagat | aaagtttcga | 1800 |
| tttctattca | tgtcttttttg | gattttgatt | tgaatttgaa | gttaaactag | agaaaatcag | 1860 |
| ctgaatcctt | acttgttata | tggtatgaaa | catctacttg | atatgtcttg | ttctgctgaa | 1920 |
| ccaaattatg | tcttgaaatc | ttagctgctt | ttgttttttgc | aggtgaattt | gtttgataga | 1980 |
| atcaagaaca | aacctttaaa | | | | | 2000 |

<210> SEQ ID NO 17
<211> LENGTH: 2000
<212> TYPE: DNA
<213> ORGANISM: Arabidopsis thaliana

<400> SEQUENCE: 17

| | | | | | | |
|---|---|---|---|---|---|---|
| agagaaaaag | agaaacaaaa | tgagacgtg | agggattttg | aagatttatt | tatgggggca | 60 |
| agtcatgtat | aatgtttggg | gaggaatttt | attaaggaag | gaaatttgaa | caagttactt | 120 |
| gtttatacat | gtacaactac | acgtaagtta | tttaaccaat | tgatatgaaa | tggtttccaa | 180 |
| tatctagatt | tgtttaattg | attcttgatt | ttttccatt | atagcttgta | gaatttctac | 240 |
| gaagatgatg | cgatttgtaa | aaccaaaatt | atagtcaaaa | gaaaagacaa | ggaaaaaggt | 300 |
| ttgaagtaaa | agagtaaatt | gagtacttgg | aataaatcta | ggtttgaagt | cgaagattca | 360 |
| acaataacaa | tataagtaat | taggtagata | aattctcata | tgtatgatga | aataaatcaa | 420 |
| taagacaaaa | aaaaaaaaa | ggttgattct | cttcttgtca | ctgttgtgag | agctttgttt | 480 |
| ttttaggtga | aatattaggg | gtcctaccc | caatgttccc | cattcattat | aatactttat | 540 |
| gtgtaaacat | aggcatatat | atagagaagt | tttgagatat | atatcaggcc | cggctcttgg | 600 |
| gaggtgctga | gtgtgctagt | gcaccgggtt | tcacttcttt | attcagtttt | ttctttatat | 660 |
| tttagggtcc | aaattttcaa | ataattgcaa | aataggattt | agttttttaaa | tatttagagt | 720 |
| tttaggtaaa | gaaatttgga | gcatagcaca | aggtccaata | atttattggg | ccggctctga | 780 |
| tatatactaa | gacactatat | agaagtttga | ttatgtcaaa | caagaaaatt | tgaatgagaa | 840 |
| gtttgaatat | agagagactt | atcaatatca | ctttagttca | acattagatg | taataacagt | 900 |
| taaacaattt | tctaaccaat | ccaaataact | caggttaagt | tcatctcaat | tatttgtttg | 960 |
| gaagtttcat | ttgaagtaca | ttaatctcaa | ttgagacgaa | tgtcatagtc | catatatttt | 1020 |
| gtgtacctcg | tcatctttgg | gccgaaggaa | caaagaaaac | ttagcccgat | taggatccat | 1080 |
| tcatatatgg | gcccatataa | ggcatttagt | gtaatagatt | tttgcatcat | catgtcttga | 1140 |
| gatttctat | tagaaaagtc | gaaacaatca | aataaaccaa | gagaaatatt | gaaagcaatc | 1200 |
| atgttggcat | tgagtaaatt | atgtaagatt | tgaattctcc | gaggaacaca | ctacgtttgt | 1260 |
| atgttgcgtt | ctaactttag | aaagattaaa | aaccataaaa | tattggtaat | cgagaaaatg | 1320 |
| aagttagatc | tttcacatgc | aatgatatgc | atatgggaca | gccaagcagt | ttatatgttg | 1380 |
| tgttgtgttg | tataatataa | gacaagatgc | tttataatta | tgtgaagcga | atattcattg | 1440 |

```
gaatagattt ccgattccac atttctttct ctttttttgg ttgtatttat aagcaatata      1500
aaaaaaatta ttatataaat atatataaag aatatatata aggttgtctt ggcgtaatta      1560
tttgagtttt atgttatatc gatctacaag taattagcgc ggctaatgat atgatacgta      1620
acgaaaagta ttttgaccaa ataattacaa agtcaatttt ttttttgtcag gagtacgtta     1680 ttgtgattgt gtttttttt tttttgtagt aattgttttc tcaagtgttt aaaccctaa        1740 tgtatgcata aaccattata acaacaacga ttttctata acttctgtaa tattaataaa       1800
agataaattt tagcatatgc taaaacgagt attaggatgc ttatctgtct ctgcctcaca      1860
aagaggatat acctctcttt cgtcttcttc agattctctc tgacggttgt taaaaatccg      1920
attataacga cgacgacacc caaatcctca caaatatata attattaatt taagcttctc     1980
tgtcaaaata aaaaggagtc                                                 2000

<210> SEQ ID NO 18
<211> LENGTH: 2000
<212> TYPE: DNA
<213> ORGANISM: Arabidopsis thaliana

<400> SEQUENCE: 18
gatgagattt aatagtcgct ccactttttt tcttttcgat attaatgatg tatgatttgt        60
tactcaggtg tccccaaact caaaagatct gagattgaag ctgcctgtga agatttagt       120 aatgtcattg ggtcttgccc cattggtaca ttgttcaaag ggacgctatc aagtggggtg      180
gagatagctg tggcttctgt tgctactgcg tctgccaaag aatggacaaa taatatagaa      240
atgcagttca gaaagaaggt atttccggtc aaccagtttt cttatatttt aaggattttg      300
atttctatca ccttatcgat tatggtttcg atgatttcag atcgaaatgt tatccaagat      360
aaaccacaag aattttgtca acccttcttgg ttactgtgaa gaagaagaac cttttcactag    420 gatcttggtc tttgaatatg catcaaacgg aacagtcttt gaacatttac actgtaagta      480
acaaagctct ttagtcatat gagtcattat tacactgtaa gttgtcagat taaaagtggg      540
aaaacaatat ttacttttgc tgcagataaa gaatcagaac acttggactg ggtaatgcgg      600
ctaagaatag caatgggcat agcttattgc cttgaccata tgcacggact caagccacct      660
atagtccaca gcaatcttct ctcatcatca gttcaactca cagaggacta cgcagtcaaa      720
attgcggatt tcaattttgg atatttaaaa ggcccatccg agacagaaag cagcaccaat      780
gcactcatag atacaaacat ctcagaaaca acacaagaag acaatgttca cagcttcggg      840
ttgctgttgt ttgaactgat gacaggaaaa ctcccagagt cagttcaaaa aggtgactcg      900
atagataccg gattggctgt cttcttgaga ggaaagacat taagggagat ggtggatccg      960
acaattgaaa gctttgacga gaagattgag aatataggtg aagtgatcaa aagctgcata    1020
agagcagacg cgaaacagag accgataatg aaggaagtca cagggagatt acgagagatc    1080
actggattat caccagacga cactatccca aaactttcac cactctggtg ggcagagctg    1140
gaagttctgt ccactgcgtg aagagacaac tactgaactt cacaaaaaaa tctgtaagta    1200
ttaatatgaa gatttgagtg aggttttttga gtctcttaga agctcttggc ttctcttttag   1260 gctactttca tctatctatc tatatataag tatggaactt agtttatata acggctttaa    1320
aattcggtgg atctatttgg tcgtttatgt cgtaaacaga aaatgtccta atcacggtaa    1380
tacccctttt tggtgtgcat aatgttggtg ggtggttact gtctttgtaa attagtgtta    1440
ctatgttctt gatatgttta atcatcaggt tctgaagtat aattcacaaa ttctgctcgt    1500
```

```
tcaaatttat ttagttgaag atggtgctac caattcaatg aataatttaa aaatgttttc      1560
gtttgtactc cactatttaa cactccacct cctaaatcca catgcaaata tcgtagctaa      1620
taatcaaaac ataatcaatc acaaaaacaa aattaatatc gctttgtgtc acatattatg      1680
ctaaaaatgt tggagtcgac atgaacaatg aagatggccc atcggtgtaa tccaaaatgg      1740
tgtcgtctga accgtcagat taaagattgc aacacacgac aatcacacat catcttctac      1800
acaatcaaat cccttcgatc gaagctcatt ggattatatt ttttttcctt cacattaaag      1860
acaaaaaaaa aaagcgaaag aaaagaagca atcgtagaga gtgattctgg gcatatgctt      1920
ggagtatctc tccttatccc tccttggggt tctcttcaaa accccttctt ccttctcctt      1980
ctgtaaccat cttcttcacc                                                  2000

<210> SEQ ID NO 19
<211> LENGTH: 33
<212> TYPE: DNA
<213> ORGANISM: Artificial sequence
<220> FEATURE:
<223> OTHER INFORMATION: PCR primer

<400> SEQUENCE: 19
cgcccgggta tggcgatttt ggattctgct ggc                                   33

<210> SEQ ID NO 20
<211> LENGTH: 33
<212> TYPE: DNA
<213> ORGANISM: Artificial sequence
<220> FEATURE:
<223> OTHER INFORMATION: PCR primer

<400> SEQUENCE: 20
gcgagctctc atgacatcga tccttttcgg ttc                                   33

<210> SEQ ID NO 21
<211> LENGTH: 403
<212> TYPE: PRT
<213> ORGANISM: Chlamydomonas reinhardtii

<400> SEQUENCE: 21

Met Val Asn Ile Pro Leu Pro Phe Phe Gly Arg Arg Ala Arg Ala
1               5                   10                  15

Gly Thr Arg Thr Ser Pro Gln Glu Pro Ala Ala Asp Lys Gln Glu Leu
            20                  25                  30

Ile Arg Leu Gln Lys Glu Val Glu Thr Leu Arg Val Ala Asn Glu Gln
        35                  40                  45

Leu Lys Glu Gln Leu Ala Ala Arg Ser Ile Arg Leu Gly Glu Tyr Leu
    50                  55                  60

Tyr Lys Trp Ser Ala Gly Leu Pro Leu Gly Ala Leu Gly Leu
65                  70                  75                  80

Gly Gly Pro Ala Ala Glu Trp Gly Leu Arg Tyr Val Leu Leu Arg Gly
                85                  90                  95

Thr Gly Leu Ala Ala Tyr Gly Ser Ala Lys Asp Thr Ala Phe Ser Pro
            100                 105                 110

Arg Asp Glu Ile Ser Val Leu Ser Cys Phe Val Ala Trp Glu Gly Leu
        115                 120                 125

Arg Ala Gly Arg Phe Trp Ala Phe Ser Val Phe Asp Ser Gly Gly Ser
    130                 135                 140

Leu Leu Leu Asp Leu Pro Arg Val Ala Glu Arg Val Leu Lys Leu Ala
145                 150                 155                 160
```

Leu Pro Ser Thr Tyr Ala Trp Leu Leu Gly Phe Tyr Cys Leu Phe His
                165                 170                 175

Leu Trp Leu Asn Val Leu Ala Glu Leu Thr Arg Phe Gly Asp Arg Glu
            180                 185                 190

Phe Tyr Lys Asp Trp Trp Asn Ala Ala Thr Val Gly Glu Tyr Trp Lys
        195                 200                 205

Leu Trp Asn Met Pro Val His Lys Trp Leu Leu Arg His Val Tyr Phe
    210                 215                 220

Pro Ala Ile Arg Ala Gly Ser Ser Arg Phe Asn Ala Ile Leu Leu Thr
225                 230                 235                 240

Phe Phe Val Ser Ala Val Phe His Glu Leu Leu Leu Gly Val Pro Leu
                245                 250                 255

His Met Val Arg Leu Trp Ala Phe Ala Gly Ile Met Phe Gln Val Pro
            260                 265                 270

Leu Ile Met Val Thr Glu Met Leu Arg Lys Lys Leu Asn Arg Asp Glu
        275                 280                 285

Leu Gly Asn Tyr Ile Phe Trp Ile Ala Phe Cys Val Val Gly Gln Pro
    290                 295                 300

Val Cys Val Leu Leu Tyr Tyr His Asp Tyr Val Val Gly Ile Arg Pro
305                 310                 315                 320

Ala Leu Leu Ala Leu Arg Gln Ala Ala Ala Val Gly Gly Ala Ala
                325                 330                 335

Ala Ala Val Gly Glu Ala Ala Ala Ala Ala Ala Ala Gly Ala Gly
            340                 345                 350

Val Ala Gly Thr Val Ala Ala Gly Val Gly Ala Ala Ala Ala Ala Ala
                355                 360                 365

Ile Gly Gly Met Leu Gly Asp Gly Gly Thr Gly Ala Ala Ala Ala Ala
            370                 375                 380

Ala Gly Val Val Ala Ala Gly Asn Cys Thr Leu Gly Ala Val Ala Cys
385                 390                 395                 400

Gly Val Ser

<210> SEQ ID NO 22
<211> LENGTH: 331
<212> TYPE: PRT
<213> ORGANISM: Chlamydomonas reinhardtii

<400> SEQUENCE: 22

Met Asn Gln Leu Glu Leu Val Met Cys Arg Leu Ala Val Ser Trp Phe
1               5                   10                  15

Leu Ile Thr Ala Ile Ser Gln Ala Trp Val Trp Pro Leu Leu Ile Gly
            20                  25                  30

Thr Leu Leu Tyr Val Gln Ser Thr Thr Leu Thr Ile Ala Phe Leu Leu
        35                  40                  45

Tyr Leu Tyr Tyr Val Val Gly Pro Gly Ser Lys Asp Asp Ala Asn
    50                  55                  60

Cys Lys Trp Lys Pro Thr Phe Arg Lys Trp His Ile Trp Lys Val Met
65                  70                  75                  80

Ala Ser Tyr Phe Pro Gly Ala Arg Leu Ile Lys Thr Ala Asp Leu Asp
                85                  90                  95

Pro Ala Gly Arg Tyr Ile Phe Val Ser His Pro His Gly Val Ile Ala
            100                 105                 110

Ile Ser Asp Trp Leu Ala Phe Ala Thr Glu Ala Leu Gly Phe Ser Lys
        115                 120                 125

-continued

Leu Phe Pro Gly Leu Asp Leu Arg Cys Ala Thr Leu Ala Ser Asn Phe
      130                 135                 140

Trp Val Pro Gly Leu Arg Glu Tyr Ile Leu Ser His Gly Met Cys Gly
145                 150                 155                 160

Val Gly Arg Asp Thr Leu Ala Arg Val Leu Thr Gly Lys Pro Gly Arg
                165                 170                 175

Ala Val Val Leu Val Val Gly Ala Ser Glu Ala Leu Leu Ala Ala
            180                 185                 190

Glu Gly Thr Tyr Asp Leu Val Leu Arg Asn Arg Lys Gly Phe Val Arg
            195                 200                 205

Leu Ala Leu Gln Thr Gly Ala Ser Leu Val Pro Val Leu Ser Tyr Gly
      210                 215                 220

Glu Thr Asp Thr Phe His Thr Tyr Ile Pro Pro Cys Ser Arg Ala
225                 230                 235                 240

Ala Ala Val Met Lys Val Leu Lys Gln Val Phe Gly Phe Ser Thr Pro
                245                 250                 255

Leu Cys Trp Gly Thr Gly Leu Phe Gly Gly Trp Gly Met Leu Ala Leu
            260                 265                 270

Gln Val Pro Leu Thr Val Val Gly Ala Pro Ile Gln Val Asp Lys
            275                 280                 285

Val Ser Ser Pro Thr Glu Ala Glu Val Ala Ala Leu His Lys Thr Tyr
290                 295                 300

Thr Glu Ala Leu Gln Lys Leu Trp Asp Asp Thr Val Asp Lys Tyr Gly
305                 310                 315                 320

Lys Gly Val Lys Arg Pro Leu Ala Ile Val Gln
                325                 330

<210> SEQ ID NO 23
<211> LENGTH: 324
<212> TYPE: PRT
<213> ORGANISM: Chlamydomonas reinhardtii

<400> SEQUENCE: 23

Met Ala Ile Asp Lys Ala Pro Thr Asn Val Arg Ile Trp Ser Asp Gly
1               5                   10                  15

Val Thr Glu Lys Gly Lys Gln Ser Ile Phe Ser Ser Leu Val Ala Met
            20                  25                  30

Leu Thr Leu Phe Ile Tyr Cys Gly Trp Met His Val Leu Leu Ala Leu
        35                  40                  45

Val Ile Leu Ser Phe Trp Tyr Arg Trp Ala Leu Val Thr Val Leu Leu
    50                  55                  60

Leu Tyr Ser Thr Leu Leu Leu Pro Pro Lys Pro Val Leu Trp Gly Pro
65                  70                  75                  80

Val Cys Arg Ser Trp Ile Phe Gln Thr Trp Arg Glu Tyr Phe Lys Phe
                85                  90                  95

Ser Tyr Val Phe Asp Glu Val Leu Asp Ser Lys Lys Tyr Ile Phe
            100                 105                 110

Ala Glu Phe Pro His Gly Val Phe Pro Met Gly Pro Leu Ile Gly Ala
        115                 120                 125

Thr Glu Cys Gln Ile Met Phe Pro Gly Phe Asp Ile Phe Gly Leu Ala
    130                 135                 140

Ala Asn Val Val Phe Thr Val Pro Phe Trp Arg His Phe Val Ala Trp
145                 150                 155                 160

Leu Gly Ser Val Pro Ala Thr Thr Arg Asp Phe Lys Arg Val Leu Lys

```
            165                 170                 175
Gln Gly Ser Val Ala Ile Val Gly Gly Ile Ala Glu Met Tyr Met
            180                 185                 190

Gln Ser Pro Thr Lys Glu Gln Ile Met Leu Lys Asp Arg Lys Gly Phe
            195                 200                 205

Val Arg Val Ala Val Glu Glu Gly Val Asp Gly Ile Val Pro Val
            210                 215                 220

Tyr His Phe Gly Asn Ser Gln Val Leu Asp Phe Gly Pro Gln Ala Met
225                 230                 235                 240

Ala Ser Val Ser Arg Arg Leu Arg Ala Ala Leu Gly Phe Leu Tyr Gly
                245                 250                 255

Val Ala Tyr Leu Pro Leu Pro Arg Arg Arg Asn Ile Tyr Met Val Cys
                260                 265                 270

Gly Lys Pro Val Pro Val Thr Arg Thr Ala Arg Asp Asp Pro Lys Phe
                275                 280                 285

Glu Glu Val Val Asp Ala Thr His Ala Ala Val Met Ala Ala Leu Gln
                290                 295                 300

Glu Ala Tyr Asp Arg His Lys Thr Glu Tyr Gly Trp Ala Asp Arg Pro
305                 310                 315                 320

Leu Val Ile Ser

<210> SEQ ID NO 24
<211> LENGTH: 346
<212> TYPE: PRT
<213> ORGANISM: Chlamydomonas reinhardtii

<400> SEQUENCE: 24

Met Ala Gly Gly Lys Ser Asn Gly Thr Gly Ala Ala Asp Ala His Val
1               5                   10                  15

Arg Thr Ser His Leu Thr Leu Lys Ala Gly Glu Asp Pro Pro Pro Asn
                20                  25                  30

Val Arg Ile Tyr Ser Asp Gly Ile Lys Pro Asp Ala Arg Gln Asn Leu
            35                  40                  45

Leu Val Gln Ile Leu Ala Gly Ile Thr Met Ser Ile Tyr Val Gly Phe
    50                  55                  60

Met Asn Tyr Phe Met Leu Leu Val Leu Ser Tyr Trp Ser Arg Ile
65                  70                  75                  80

Cys Arg Tyr Val Val Leu Ala Leu Leu Gly Thr Leu Ala Leu Pro Cys
                85                  90                  95

Lys Pro Val Leu Trp Pro Ala Phe Asn Lys Leu Trp Ile Phe Lys Thr
            100                 105                 110

Trp Arg His Tyr Phe His Tyr Ser Phe Leu Ile Glu Glu Pro Leu Asp
        115                 120                 125

Pro Asn Lys Arg Tyr Ile Phe Val Glu Phe Pro His Gly Ala Phe Pro
    130                 135                 140

Ile Gly Pro Ile Val Ala Gly Thr Leu Met Gln Thr Leu Phe Pro His
145                 150                 155                 160

Met Met Ile Tyr Ser Val Ala Ala Ser Val Val Phe Tyr Ile Pro Phe
                165                 170                 175

Trp Arg His Phe Ile Thr Trp Ile Gly Ser Val Pro Ala Thr Pro Gly
            180                 185                 190

Asn Phe Lys Arg Leu Leu Lys Lys Gly Ser Val Ala Val Val Gly
        195                 200                 205

Gly Ile Ala Glu Met Tyr Met Gly Asn Lys Lys Lys Glu Arg Ile Lys
```

```
                    210                 215                 220
Leu Val Gly Arg Arg Gly Phe Ala Arg Ile Ala Leu Glu Glu Gln Val
225                 230                 235                 240

Asp Gly Ile Val Cys Val Tyr Tyr Phe Gly Gln Ser Gln Val Leu Asp
                    245                 250                 255

Phe Gly Pro Ser Trp Leu Ala Asp Phe Ser Arg Arg Met Arg Thr Ser
                260                 265                 270

Phe Gly Tyr Leu Thr Gly Trp Met Gly Leu Pro Val Pro Arg Pro Ile
            275                 280                 285

Pro Ile Tyr Met Val Asn Gly Lys Pro Ile Pro Val Pro Lys Val Ala
        290                 295                 300

Arg Asp Ser Pro Glu Phe Asp Lys Glu Val Asp Lys Leu Leu Asp Ala
305                 310                 315                 320

Thr Ile Thr Glu Leu Gly Glu Met Tyr Asn Arg His Arg Gly Glu Tyr
                    325                 330                 335

Gly Trp Gly Asp Arg Pro Leu Ser Ile Glu
                340                 345

<210> SEQ ID NO 25
<211> LENGTH: 327
<212> TYPE: PRT
<213> ORGANISM: Chlamydomonas reinhardtii

<400> SEQUENCE: 25

Met Pro Leu Ala Lys Leu Arg Asn Val Val Leu Glu Tyr Ala Ala Ile
1               5                   10                  15

Ala Ile Tyr Val Ser Ala Ile Tyr Thr Ser Val Val Leu Leu Pro Ser
                20                  25                  30

Ala Leu Ala Leu Phe Tyr Leu Phe Gly Ala Thr Ser Pro Ser Ala Trp
            35                  40                  45

Leu Leu Leu Ala Ala Phe Leu Ala Leu Thr Phe Thr Pro Leu Gln Leu
        50                  55                  60

Thr Thr Gly Ala Leu Ser Glu Arg Phe Val Gln Phe Ser Val Ala Arg
65                  70                  75                  80

Ala Ala Ala Tyr Phe Pro Thr Arg Val Val Val Thr Asp Pro Glu Ala
                85                  90                  95

Phe Arg Thr Asp Arg Gly Tyr Leu Phe Gly Phe Cys Pro His Ser Ala
                100                 105                 110

Leu Pro Ile Ala Leu Pro Ile Ala Phe Ala Thr Thr Ser Pro Leu Leu
            115                 120                 125

Pro Lys Glu Leu Arg Gly Arg Thr His Gly Leu Ala Ser Ser Val Cys
        130                 135                 140

Phe Ser Ala Pro Ile Val Arg Gln Leu Tyr Trp Trp Leu Gly Val Arg
145                 150                 155                 160

Pro Ala Thr Arg Gln Ser Ile Ser Gly Leu Leu Arg Ala Arg Lys Val
                165                 170                 175

Ala Val Leu Val Pro Gly Gly Val Gln Glu Val Leu Asn Met Glu His
                180                 185                 190

Gly Lys Glu Val Ala Tyr Leu Ser Ser Arg Thr Gly Phe Val Arg Leu
            195                 200                 205

Ala Val Gln His Gly Ala Pro Leu Val Pro Val Trp Ala Phe Gly Gln
        210                 215                 220

Thr Arg Ala Tyr Ser Trp Phe Arg Pro Gly Pro Pro Leu Val Pro Thr
225                 230                 235                 240
```

Trp Leu Val Glu Arg Ile Ser Arg Ala Ala Gly Ala Val Pro Ile Gly
            245                 250                 255

Met Phe Gly Gln Tyr Gly Thr Pro Met Pro His Arg Glu Pro Leu Thr
        260                 265                 270

Ile Val Val Gly Arg Pro Ile Pro Val Pro Glu Leu Ala Pro Gly Gln
    275                 280                 285

Leu Glu Pro Glu Pro Glu Val Leu Ala Ala Leu Leu Lys Arg Phe Thr
290                 295                 300

Asp Asp Leu Gln Ala Leu Tyr Asp Lys His Lys Ala Gln Phe Gly Lys
305                 310                 315                 320

Gly Glu Glu Leu Val Ile Met
            325

<210> SEQ ID NO 26
<211> LENGTH: 856
<212> TYPE: PRT
<213> ORGANISM: Chlamydomonas reinhardtii

<400> SEQUENCE: 26

Met Ser Leu Thr Pro Glu Leu Ile Thr Gln Phe Gly Leu Leu Gly Lys
1               5                   10                  15

Val Arg Thr Gly His Pro Val Leu Asp Ala Val Leu Cys Met Leu Leu
            20                  25                  30

Pro Leu Leu Leu Arg Trp Ala Gln Pro Arg Leu Asn Arg Trp Ala Leu
        35                  40                  45

Leu Ala Ala Ala Ala Leu Arg Arg Trp Trp Ser Gly Glu Ala Gly Cys
    50                  55                  60

Lys Glu Val Val Arg Val Ile Glu His Val Ala Ala Glu Asp Gly Tyr
65                  70                  75                  80

Tyr Tyr Asp Pro Asp Gly Gln Pro Ala Asn Ala Ile Leu Gln Arg Ala
                85                  90                  95

Leu Leu Ala Tyr Lys Arg Arg Arg Leu Ala Ala Ala Gly Gly Asp
            100                 105                 110

Ala Asp Ser Asp Ser Gly Asp Glu Asp Ser Ala Ala Gly Ser Ser Ser
        115                 120                 125

Lys Ser Ser Asp Cys Gly Ser Ser Val Gly Ala Ala Lys Gln Arg Glu
    130                 135                 140

Ala Ala Ala Tyr Gly Leu Asn Leu Ala Pro Pro Val Arg Val Trp Gln
145                 150                 155                 160

Glu Leu Gly Asn Gly Val Glu Phe Met Arg Tyr Thr Tyr Thr His Asp
                165                 170                 175

Ser Ser Thr Glu Lys Arg Arg Arg Ile Ala Ser Val Ile Lys Leu Arg
            180                 185                 190

Ser Arg Ala Pro Asp Gly Ala Arg Arg Val Ser Asp Leu Ile Thr Ala
        195                 200                 205

Ala Leu Gln Arg Tyr Arg Leu Ser Gly Glu Lys Thr Phe Ala Ser Phe
    210                 215                 220

Phe His Pro Ala Lys Ser Glu Val Leu Arg Leu Val Gly Gln Phe Glu
225                 230                 235                 240

Gly Arg Gln Gly Arg Phe Ser Val Pro Gly Tyr Pro Lys Leu Gly
                245                 250                 255

Leu Leu Leu Tyr Gly Pro Pro Gly Thr Gly Lys Thr Ser Leu Ile Lys
            260                 265                 270

Ala Leu Ala Gln Leu Thr Gly Arg Ser Val Val Ser Val Pro Leu Ala
        275                 280                 285

```
Arg Ile Ala Thr Asn Gln Gln Leu Met Asp Ile Met Phe Asp Thr Arg
            290                 295                 300

Val Leu Leu Gln Arg Arg His Asn Ser Gly Ser Gly Gly Gly Gly Ser
305                 310                 315                 320

Lys Arg Ser Gly Gly Ser Pro Pro Asn Asn Asp Phe Gly Pro Met Cys
                325                 330                 335

Glu Ala Glu Ala Val Ala Leu Ala Ala Ala Leu Ala Glu Ser Met Ala
            340                 345                 350

Gly Ser Pro Asn Ala Ala Ala Thr Ala Thr Ala Asn His Ala Ala Thr
            355                 360                 365

Asp Tyr Ala Ala Gly Tyr Ser Met Tyr Ser Ser His Arg Trp Pro Cys
370                 375                 380

Lys Asp Ala Leu Asn Leu Ala Gly Ile Leu Asn Val Leu Asp Gly Val
385                 390                 395                 400

Val Asp Thr Pro Gly Arg Ile Val Ile Leu Thr Thr Asn Cys Pro Asp
                405                 410                 415

Ser Leu Asp Pro Ala Leu Ile Arg Pro Gly Arg Ile Asn Lys Val Leu
                420                 425                 430

His Leu Gly Arg Leu Arg Leu Ala Glu Ala Thr Ala Met Met Arg His
            435                 440                 445

Tyr Cys Phe Pro Ala Gly Gly Asp Met Ala Ser Ala Gly Met Asp Gly
450                 455                 460

Leu Thr Ser Arg Thr Ala Phe Leu Thr Asp Ala Ala Cys Trp Phe Arg
465                 470                 475                 480

His Met Glu Leu Asp Thr Val Ser Gly Leu Asp Pro Glu Gly Ile Lys
                485                 490                 495

Leu Arg Ala Ala Leu Gly Leu Glu Ala Val Asp Tyr Phe Ile Gln Gly
                500                 505                 510

Tyr Trp Val Trp Gly Lys Leu Val Glu Ala Leu Ala Asp Val Gly Tyr
            515                 520                 525

Asp Ser Asn Ser Leu Val Ser Met Pro Tyr Asp Trp Arg Leu Ala Val
530                 535                 540

Pro Leu Leu Glu Glu Arg Asp Gly Tyr Tyr Thr Arg Leu Arg Arg Thr
545                 550                 555                 560

Ile Glu Gln Leu Val Glu Leu Thr Gly Glu Arg Val Val Val Thr Ser
                565                 570                 575

His Ser Tyr Gly Glu Asn Val Val Arg Gln Asn Ser Arg Arg Arg Arg
            580                 585                 590

Leu Cys Gly Ala Ser Cys Arg Ala Gly Glu Thr Arg Asp Thr Ala Gln
            595                 600                 605

Leu Gly Ala Leu Ala Gly Phe Leu Thr Ser Asn Met Val Pro Arg Ala
            610                 615                 620

Ala Arg Thr Arg Val Trp Arg Ser Trp Gly Ala Ser Tyr Ala Met Leu
625                 630                 635                 640

Pro Val Gly Gly Pro Gly Val Trp Gly Asn Ala Ser Trp Ala Pro Asp
                645                 650                 655

Asp Thr Pro Glu Met Arg Ala Asn Arg Arg Thr Phe Gly Ser Met Val
                660                 665                 670

Ser Leu Trp Pro His Asn Trp Gln Ala Leu Met Ala Ala Ala Pro Gln
            675                 680                 685

Gln Gln Arg Glu Gln Leu Ser Gln Leu Val Ala Glu Val Thr Arg Leu
690                 695                 700
```

```
Asp Val Ser Gly Phe Ile Ala Leu Leu Arg Glu Val Gly Gly Pro Leu
705                 710                 715                 720

Val Ser Ala Asn Ile Ala Gln Trp Gly Ala Leu Gln Leu Pro Ala Glu
            725                 730                 735

Glu Ala Ala Glu Ala Asp Val Gly Val His Ile Ser Asp Gly Asp Gly
        740                 745                 750

Thr Val Pro Leu Leu Ser Leu Gly Leu Met Cys Arg Gly Gly Trp Arg
    755                 760                 765

Glu Ala Gly His Leu Asn Pro Gly Ala Met Arg Val Gly Ala Gly
770                 775                 780

Arg Val Thr Arg Glu Tyr Lys His Lys Ala Val Ser Met Leu Gln Asp
785                 790                 795                 800

Ala Arg Gly Gly Pro Ala Ala Ala His Ile Asp Ile Leu Gly Asn
            805                 810                 815

Asp Ala Val Leu Arg Asp Val Ile Thr Val Ala Gly Arg Ala Asp
        820                 825                 830

Glu Leu Ala Asp Ile Val Val Ser Asp Ile Asp Arg Ile Ala Ala Ala
    835                 840                 845

Val Asp Trp Ala Ala Leu Ala Ala
    850                 855

<210> SEQ ID NO 27
<211> LENGTH: 34
<212> TYPE: DNA
<213> ORGANISM: Artificial sequence
<220> FEATURE:
<223> OTHER INFORMATION: PCR primer

<400> SEQUENCE: 27
gccccgggta tgggtggttc cagagagttc cgag                              34

<210> SEQ ID NO 28
<211> LENGTH: 32
<212> TYPE: DNA
<213> ORGANISM: Artificial sequence
<220> FEATURE:
<223> OTHER INFORMATION: PCR primer

<400> SEQUENCE: 28
gcgagctctc aaagaatttt cagctcaaga tc                                32

<210> SEQ ID NO 29
<211> LENGTH: 32
<212> TYPE: DNA
<213> ORGANISM: Artificial sequence
<220> FEATURE:
<223> OTHER INFORMATION: PCR primer

<400> SEQUENCE: 29
cgcccgggta tgcccttat catcggaaaa ag                                 32

<210> SEQ ID NO 30
<211> LENGTH: 32
<212> TYPE: DNA
<213> ORGANISM: Artificial sequence
<220> FEATURE:
<223> OTHER INFORMATION: PCR primer

<400> SEQUENCE: 30
gcgagctctc acagcttcag gtcaatacgc tc                                32
```

FUSED GENE, VECTOR, TRANSGENIC PLANT, METHOD FOR MANUFACTURING VEGETABLE FAT OR OIL, METHOD FOR CONSTRUCTING TRANSGENIC PLANT, AND KIT FOR CONSTRUCTING TRANSGENIC PLANT

CROSS-REFERENCE TO RELATED APPLICATIONS

This application is a 35 U.S.C. § 371 United States national phase application of PCT International Application No. PCT/JP2014/072296, filed Aug. 26, 2014, which claims the benefit of priority to Japanese Patent Application No. 2013-177774, filed Aug. 29, 2013. The contents of the above-referenced applications are incorporated herein by reference in their entireties.

The present invention relates to a fused gene, a vector, a transgenic plant, a method for manufacturing vegetable fat or oil, a method for constructing a transgenic plant, and a kit for constructing a transgenic plant.

INCORPORATION BY REFERENCE OF MATERIAL SUBMITTED ELECTRONICALLY

Incorporated by reference in its entirety is a computer-readable sequence listing submitted concurrently herewith and identified as follows: One 76.0 KB ASCII (Text) file named "OSP62383 ST25.txt."

BACKGROUND ART

Every year, one hundred million tons or more of vegetable fat or oil is used around the world for foods such as margarine, shortening, dressing, and hydrogenated edible oil, for fuels, or for industrial use such as lubricating oil or raw materials of surfactants. Due to the increase in the world population or the like, a demand for the vegetable fat or oil keeps increasing. The production of vegetable fat or oil focused on palm oil and soybean oil increased by about 1.5 times between 2001 and 2008. It is considered that the increase in production may result from the promotion of forestation, breed improvements, and the like in the main production areas such as Malaysia or Indonesia, or may be greatly affected by policies including grants that are implemented as the use of biodiesels is increasing, particularly in Europe.

However, for example, regarding palm oil or coconut oil, the area where the plants can be cultivated is limited to a partial area such as Southeast Asia, and biological diversity has to be protected. Because of these issues, it is not desirable for expansion of plantations due to deforestation, and there is a demand for increasing the production of fat or oil per unit plant.

Under the circumstances described above, the inventors of the present invention have developed a method for manufacturing vegetable fat or oil by using plants cultivated in a phosphorus-deficient state or plants suffering from phosphorus deficiency (PTL 1). Furthermore, the inventors have developed a method for manufacturing vegetable fat or oil by cultivating mutated plants in which starch biosynthesis is inhibited (PTL 2).

CITATION LIST

Patent Literature

[PTL 1] Japanese Unexamined Patent Application, First Publication No. 2012-7146

[PTL 2] Japanese Unexamined Patent Application, First Publication No. 2012-153833

SUMMARY OF INVENTION

Technical Problem

In the plants used in the methods for manufacturing vegetable fat or oil described in PTL 1 and 2, vegetable fat or oil could be accumulated more to a certain degree than in plants under normal conditions or wild-type plants. However, the production technique of the vegetable fat or oil using plants needs to be further investigated.

The present invention has been made in consideration of the circumstances described above, and an object thereof is to provide a transgenic plant which makes it possible to efficiently manufacture vegetable fat or oil while continuing photosynthesis of the plant, a fused gene, a vector which makes it possible to construct the transgenic plant, a kit which includes the vector, a method for constructing the transgenic plant, and a method for manufacturing vegetable fat or oil by cultivating the transgenic plant.

Solution to Problem

In order to achieve the above object, the inventors of the present invention conducted intensive research. As a result, they obtained knowledge that by controlling the expression of a nucleic acid sequence affecting the biosynthesis or accumulation of neutral lipid by using a phosphorus deficiency-responsive transcription control sequence, it is possible to markedly increase the amount of fat or oil accumulated in a plant while favorably growing the plant. Based on this knowledge, the inventors accomplished the present invention. That is, the present invention is as follows.

(1) A fused gene including a nucleic acid sequence which affects the biosynthesis or accumulation of neutral lipid and a phosphorus deficiency-responsive expression control sequence which is operably linked to the nucleic acid sequence and controls the expression of the nucleic acid sequence.

(2) The fused gene described in (1), in which the nucleic acid sequence is a nucleic acid sequence encoding a protein which affects the biosynthesis or accumulation of neutral lipid.

(3) The fused gene described in (2), in which the protein which affects the biosynthesis or accumulation of neutral lipid is DGAT or PDAT.

(4) The fused gene described in any one of (1) to (3), in which the control sequence is a sequence of a promoter of a gene selected from the group consisting of a monogalactosyldiacylglycerol synthase gene, a phospholipase C gene, a phospholipase D gene, a phosphatidic acid phosphohydrolase gene, a sulfoquinovosyldiacylglycerol synthase gene, a UDP-sulfoquinovose synthase gene, an SQDG synthase gene, and a UDP-glucose pyrophosphorylase gene.

(5) The fused gene described in any one of (2) to (4), in which the protein which affects the biosynthesis or accumulation of neutral lipid is a protein including an amino acid sequence of any of the following (a) to (d):

(a) a protein including an amino acid sequence represented by any of SEQ ID NOS:1 to 5, (b) a protein including an amino acid sequence which is obtained by the deletion, substitution, or addition of one to several amino acids in the amino acid sequence represented by any of SEQ ID NOS: 1 to 5, (c) a protein including an amino acid sequence which shares identity of equal to or higher than 90% with the amino acid sequence represented by any of SEQ ID NOS: 1 to 5 and has acyltransferase activity, and (d) a protein including an amino acid sequence which shares identity of equal to or higher than 25% with the amino acid sequence represented by any of SEQ ID NOS: 1 to 5, belonging to a membrane-bound O-acyltransferase (MBOAT) family, and having acyltransferase activity.

(6) A vector containing the fused gene described in any one of (1) to (5).

(7) A transgenic plant containing the fused gene described in any one of (1) to (5).

(8) A transgenic plant obtained by introducing the vector described in (6) into a host.

(9) The transgenic plant described in (7) or (8) that is a plant in which at least one function selected from the group consisting of carbohydrate metabolism, starch biosynthesis, and membrane lipid metabolism is depressed or inhibited.

(10) A transgenic plant obtained by the hybridization between the transgenic plant described in (7) or (8) and a plant in which at least one function selected from the group consisting of carbohydrate metabolism, starch biosynthesis, and membrane lipid metabolism is depressed or inhibited.

(11) A method for manufacturing vegetable fat or oil, including a cultivation step of cultivating the transgenic plant described in any one of (7) to (10).

(12) The method for manufacturing vegetable fat or oil described in (11), in which the cultivation step is a step of cultivating the transgenic plant in a phosphorus-deficient state.

(13) The method for manufacturing vegetable fat or oil described in (12), in which the cultivating in the phosphorus-deficient state is a step of cultivating a plant including fully grown tissue by transplanting the plant into a phosphorus-deficient medium, by replacing a medium of the plant with a phosphorus-deficient medium, or by maintaining the phosphorus-deficient state that is created in a medium in the process of cultivation.

(14) The method for manufacturing vegetable fat or oil described in (11), in which the cultivation step is a step of cultivating the transgenic plant as a plant suffering from phosphorus deficiency.

(15) The method for manufacturing vegetable fat or oil described in (14), in which the plant suffering from phosphorus deficiency is a plant in which a function of transporting phosphoric acid is depressed or inhibited.

(16) A method for constructing a transgenic plant, including a step of introducing the vector described in (6) into a plant.

(17) A kit for constructing a transgenic plant, including the vector described in (6).

Advantageous Effects of Invention

According to the present invention, it is possible to provide a transgenic plant which makes it possible to more efficiently manufacture vegetable fat or oil compared to the plants known in the related art that are cultivated in a phosphorus-deficient state or suffer from phosphorus deficiency, and to provide a more efficient method for manufacturing fat or oil.

DESCRIPTION OF EMBODIMENTS

<<Fused Gene>>

Figure 1A:
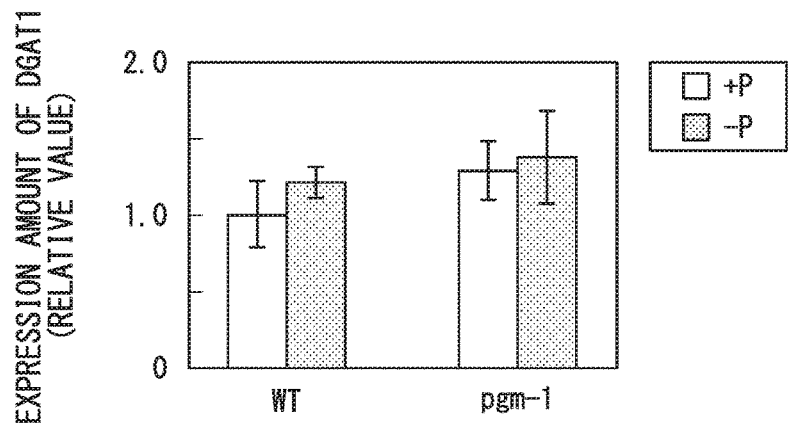
FIG. 1A is a graph showing the expression amount (relative value) of a DGAT1 gene in an *Arabidopsis thaliana* wild strain and a pgm-1 mutant strain cultivated using a medium not containing soluble phosphoric acid and a medium containing 1 mM soluble phosphoric acid.

The fused gene of the present invention includes a nucleic acid sequence which affects the biosynthesis or accumulation of neutral lipid and a phosphorus deficiency-responsive expression control sequence which is operably linked to the nucleic acid sequence and controls the expression of the nucleic acid sequence.

To "affect the biosynthesis or accumulation of neutral lipid" means increasing the amount of biosynthesized neutral lipid, increasing the accumulation amount of neutral lipid, or modifying the composition of neutral lipid. The neutral lipid may be any of monoacylglycerol, diacylglycerol, and triacylglycerol.

The "nucleic acid sequence which affects the biosynthesis or accumulation of neutral lipid" includes a nucleic acid sequence which exerts an influence as a nucleic acid such as by means of RNA interference (RNAi) and a nucleic acid which exerts an influence as a protein encoded by the nucleic acid sequence. That is, the nucleic acid sequence which is included in the fused gene of the present invention and affects the biosynthesis or accumulation of neutral lipid may be a nucleic acid sequence encoding a protein which affects the biosynthesis or accumulation of neutral lipid. As the nucleic acid sequence, a DNA sequence is preferable.

The "nucleic acid sequence which affects the biosynthesis or accumulation of neutral lipid" or the "protein which affects the biosynthesis or accumulation of neutral lipid" refers to a nucleic acid or protein which can increase the amount of neutral lipid synthesized or accumulated in the entirety or any portion of a plant compared to the original amount of neutral lipid in the host, and a nucleic acid sequence or protein which can modify the composition of neutral lipid such that the neutral lipid has a composition different from the original composition thereof, by control of the expression of the nucleic acid or protein in a plant.

It is preferable that an expression control sequence included in the fused gene of the present invention and a structural gene sequence included in the fused gene of the present invention be derived from different genes.

In a biosynthesis pathway of neutral lipid, for example, lysophosphatidic acid (LPA) is synthesized through a reaction between glycerol-3-phosphate (G3P) and a fatty acid; phosphatidic acid (PA) is synthesized through a reaction between LPA and a fatty acid; diacylglycerol (DAG) is synthesized as a result of dephosphorylation of PA by phosphatidic acid phosphatase; and triacylglycerol is synthesized from DAG by diacylglycerol acyltransferase (DGAT) or phospholipid: diacylglycerol acyltransferase (PDAT). Therefore, preferred examples of the protein which can increase the amount of neutral lipid include DGAT or PDAT involved in the pathway described above.

That is, the protein which can increase the amount of neutral lipid synthesized and affects the biosynthesis of the neutral lipid is preferably a protein including an amino acid sequence of any of the following (a) to (d).

(a) A protein including an amino acid sequence represented by any of SEQ ID NOS: 1 to 5

(b) A protein including an amino acid sequence which is obtained by the deletion, substitution, or addition of one to several amino acids in the amino acid sequence represented by any of SEQ ID NOS: 1 to 5

(c) A protein including an amino acid sequence which shares identity of equal to or higher than 90% with the amino acid sequence represented by any of SEQ ID NOS: 1 to 5 and has acyltransferase activity (d) A protein including an amino acid sequence which shares identity of equal to or higher than 25% with the amino acid sequence represented by any of SEQ ID NOS: 1 to 5, belonging to a membrane-bound O-acyltransferase (MBOAT) family, and having acyltransferase activity Furthermore, the protein which increases the amount of neutral lipid synthesized and affects the biosynthesis of the neutral lipid is preferably a protein which includes an amino acid sequence of any of the following (a) to (c), belongs to a membrane-bound O-acyltransferase (MBOAT) family, and has acyltransferase activity.

(a) An amino acid sequence which is represented by any of SEQ ID NOS: 1 to 5

(b) An amino acid sequence which is obtained by the deletion, substitution, or addition of one to several amino acids in the amino acid sequence represented by any of SEQ ID NOS: 1 to 5

(c) An amino acid sequence which shares identity of equal to or higher than 25% with the amino acid sequence represented by any of SEQ ID NOS: 1 to 5

A DGAT1 gene (AGI code: At2g19450) of *Arabidopsis thaliana* encodes a protein including the amino acid sequence represented by SEQ ID NO: 1. A DGAT2 gene (AGI code: At3g51520) of *Arabidopsis thaliana* encodes a protein including the amino acid sequence represented by SEQ ID NO: 2. A DGAT3 gene (AGI code: At1g48300) of *Arabidopsis thaliana* encodes a protein including the amino acid sequence represented by SEQ ID NO: 3. A DGAT4 gene (AGI code: At3g26840) of *Arabidopsis thaliana* encodes a protein including the amino acid sequence represented by SEQ ID NO: 4. A PDAT gene (AGI code: At5g13640) of *Arabidopsis thaliana* encodes a protein including the amino acid sequence represented by SEQ ID NO: 5.

The DGAT gene and the PDAT gene include a PLN02401 domain, an LPLAT_MGAT_Like domain, a PLN02517 domain, or an MBOAT superfamily motif, which are assumed to be involved in the acyltransferase activity.

Examples of (b) described above include a protein having a mutation (deletion, insertion, substitution, or addition) in a region other than the aforementioned domains or a protein having a mutation which occurs in the aforementioned domains and retains the acyltransferase activity.

Herein, the number of amino acids which may be deleted, inserted, substituted, or added is preferably 1 to 30, preferably 1 to 20, more preferably 1 to 10, and still more preferably 1 to 5.

(c) or (d) described above is an amino acid sequence which preferably shares identity of equal to or higher than 25%, 40%, or 50%, more preferably shares identity of equal to or higher than 60%, 70%, or 80%, even more preferably shares identity of equal to or higher than 90% or 95%, and particularly preferably shares identity of equal to or higher than 98% with the amino acid sequences represented by SEQ ID NOS: 1 to 3.

It is preferable that the identity be within the above range for the following reasons, for example. CrDGAT1 of *Chlamydomonas reinhardtii* represented by SEQ ID NO: 21 is an orthologue of AtDGAT1 of *Arabidopsis thaliana*, and the amino acid sequences thereof share identity of 60%.

Furthermore, CrDGTT1 of *Chlamydomonas reinhardtii* represented by SEQ ID NO: 22 is an orthologue of AtDGAT2 of *Arabidopsis thaliana*, and is known to retain the acyltransferase activity (Hung et al. 2013 FEBS let, Sanjaya et al. 2013 Plant Cell). The amino acid sequence identity shared between CrDGTT1 of *Chlamydomonas reinhardtii* and AtDGAT2 of *Arabidopsis thaliana* is 29%.

In addition, the orthologues retaining the acyltransferase activity share identity with the following genes, for example.

The amino acid sequence identity shared between CrDGTT2 of *Chlamydomonas reinhardtii* represented by SEQ ID NO: 23 and AtDGAT2 of *Arabidopsis thaliana* is 31%.

The amino acid sequence identity shared between CrDGTT3 of *Chlamydomonas reinhardtii* represented by SEQ ID NO: 24 and AtDGAT2 of *Arabidopsis thaliana* is 35%.

The amino acid sequence identity shared between CrDGTT4 of *Chlamydomonas reinhardtii* represented by SEQ ID NO: 25 and AtDGAT2 of *Arabidopsis thaliana* is 35%.

The amino acid sequence identity shared between CrPDAT of *Chlamydomonas reinhardtii* represented by SEQ ID NO: 26 and AtPDAT of *Arabidopsis thaliana* is 31%.

Likewise, examples of genes encoding the aforementioned proteins that can increase the amount of neutral lipid include genes which are composed of one of the following DNA and encode proteins having acyltransferase activity.

The following base sequences represented by SEQ ID NOS: 6 to 10 are base sequences of a DGAT1 gene, a DGAT2 gene, and a PDAT gene of *Arabidopsis thaliana* respectively.

(d) DNA including a base sequence represented by one of SEQ ID NOS: 6 to 10

(e) DNA including a base sequence which preferably shares identity of equal to or higher than 25%, 40%, or 50%, more preferably shares identity of equal to or higher than 60%, 70%, or 80%, even more preferably shares identity of equal to or higher than 90%, and particularly preferably shares identity of equal to or higher than 98% with the base sequence represented by one of SEQ ID NOS: 6 to 10

(f) DNA including a base sequence which can be hybridized with DNA including a base sequence complementary to the DNA including the base sequence represented by one of SEQ ID NOS: 6 to 10 under stringent conditions Examples of the proteins that can increase the amount of neutral lipid include phospholipase D, which is a membrane lipid lipase (there is a report regarding PLD α1 in Liu et al 2014 BMC Plan Biol), wrinkled 1 (WRI1), which is a transcription factor positively controlling fatty acid synthesis, an MYB-type transcription factor (there is a report regarding GmMYB73 in Liu et al 2014 BMC Plant Biol.), LEAFY COTYLEDON2 (LEC2) (Kim et al 2013 FEBS Open Bio), and the like. TAG lipase SDP1, which negatively controls fatty acid synthesis, and GLABRA2 (GL2), which is a transcription factor negatively controlling the expression amount of PLD α1, can also increase the amount of neutral lipid by a method of negatively controlling the expression of the proteins.

Examples of the protein which can modify the composition of neutral lipid include a fatty acid elongase, a fatty acid desaturase, and the like. Specific examples thereof include acyl-ACP thioesterase genes (FATA and FATB) and oleic acid desaturase genes (FAD2 and FAD3).

Examples of the nucleic acid sequence which affects the biosynthesis or accumulation of neutral lipid include sequences of an RNA interference (RNAi)-inducing nucleic acid, an antisense nucleic acid, and ribozyme for any one or more factors selected from the group consisting of a TAG lipase, the aforementioned GL2, a fatty acid elongase, and a fatty acid desaturase.

The "phosphorus deficiency-responsive expression control sequence which controls the expression of the nucleic acid sequence" included in the fused gene of the present invention is not particularly limited as long as it is a sequence which can change the expression of the nucleic acid sequence, whose expression can be controlled by the control sequence, in response to the phosphorus-deficient state. The control sequence includes an enhancer domain, a promoter sequence, and the like and is preferably a promoter sequence. To be "operably linked to the nucleic acid sequence" means that the phosphorus deficiency-responsive expression control sequence is disposed so as to control the expression of the nucleic acid sequence. To "control the expression" means not only the act of increasing the expression but also the act of exerting an influence such as decreasing the expression and shifting the expression timing. Herein, to "control the expression of the nucleic acid" includes the expression of a nucleic acid such as mRNA, miRNA, antisense RNA, or siRNA derived from the nucleic acid sequence and the expression of a protein translated by the nucleic acid sequence.

The phosphorus deficiency-responsive promoter sequence can be investigated by a known reporter assay using a reporter gene. The reporter gene is not particularly limited as long as the expression thereof can be detected, and examples thereof include GUS, GFP, and the like that are generally used by those skilled in the art.

Whether a promoter sequence is responsive to phosphorus deficiency can be checked by the following method, for example. A transgenic plant having a base sequence which is bonded to the downstream of the promoter sequence such that the expression of a reporter gene sequence can be controlled is constructed; the transgenic plant is cultivated in media containing phosphorus at various concentrations; and the expression of the reporter gene in the plant is detected. At this time, the normal phosphorus concentration in media used for comparison is within a range of 0.1 mM to 1 mM, for example. Furthermore, as the investigation method, the following method is used, for example. An expression level of the reporter gene in the plant cultivated at the normal phosphorus concentration is compared with an expression level of the reporter gene in the plant cultivated at a phosphorus concentration lower than the normal phosphorus concentration, and a promoter sequence showing a high expression level in the plant cultivated at low phosphorus concentration is selected.

Specifically, examples of the phosphorus deficiency-responsive promoter sequence include sequences of promoters of a monogalactosyldiacylglycerol synthase gene, a phospholipase C gene, a phospholipase D gene, a phosphatidic acid phosphohydrolase gene, a sulfoquinovosyldiacylglycerol synthase gene, a UDP-sulfoquinovose synthase gene, an SQDG synthase gene, and a UDP-glucose pyrophosphorylase gene.

More specifically, examples of the phosphorus deficiency-responsive promoter sequence include promoter sequences of the following genes derived from *Arabidopsis thaliana*, such as a promoter sequence (SEQ ID NO: 11) of a monogalactosyldiacylglycerol synthase 2 (MGD2) gene (AGI code: At5g20410), a promoter sequence (SEQ ID NO: 12) of an MGD3 gene (AGI code: At2g11810), a promoter sequence (SEQ ID NO: 13) of a phospholipase C5 (NPC5) gene (AGI code: At3g03540), a promoter sequence (SEQ ID NO: 14) of a phospholipase D ζ2 (zeta 2) (PLD ζ2) gene (AGI code: At3g05630), a promoter sequence (SEQ ID NO: 15) of a phosphatidic acid phosphohydrolase 1 (PAH1) gene (AGI code: At3g09560), a promoter sequence (SEQ ID NO: 16) of a UDP-sulfoquinovose synthase (SQD1) gene (AGI code: At4g33030), a promoter sequence (SEQ ID NO: 17) of an SQDG synthase (SQD2) gene (AGI code: At5g01220), and a promoter sequence (SEQ ID NO: 18) of a UDP-glucose pyrophosphorylase 3 (UGP3) gene.

Examples of the phosphorus deficiency-responsive promoter sequence also include a promoter sequence which preferably shares identity of, for example, equal to or higher than 50%, 60%, 70%, 80%, or 88%, more preferably shares identity of equal to or higher than 90%, and even more preferably shares identity of equal to or higher than 98% with the base sequence represented by any of SEQ ID NOS: 11 to 18 or with a partial sequence of the base sequence represented by any of SEQ ID NOS: 11 to 18 that is responsive to phosphorus deficiency and can control the expression of the nucleic acid sequence affecting the biosynthesis or accumulation of neutral lipid. The examples also include a promoter sequence including a base sequence which can be hybridized under stringent conditions with DNA including the complementary base sequence of the base sequence represented by any of SEQ ID NOS: 11 to 18 or with DNA which includes complementary base sequence of a partial sequence of the base sequence represented by any of SEQ ID NOS: 11 to 18, is responsive to phosphorus deficiency, and being able to control the expression of the nucleic acid sequence affecting the biosynthesis or accumu- Specific examples of a preferred combination of the nucleic acid sequence which is included in the fused gene of the present invention and affects the biosynthesis or accumulation of neutral lipid, and the phosphorus deficiency-responsive expression control sequence which is operably linked to the nucleic acid sequence and controls the expression of the nucleic acid include the following fused genes.

A fused gene including a DNA sequence that encodes a DGAT gene and a sequence of a promoter of an MGD2 gene that is operably linked to the DNA sequence and controls the expression of the DNA sequence A fused gene including a DNA sequence that encodes a DGAT gene and a sequence of a promoter of an MGD3 gene that is operably linked to the DNA sequence and controls the expression of the DNA sequence A fused gene including a DNA sequence that encodes a PDAT gene and a sequence of a promoter of an MGD2 gene that is operably linked to the DNA sequence and controls the expression of the DNA sequence A fused gene including a DNA sequence that encodes a PDAT gene and a sequence of a promoter of an MGD3 gene that is operably linked to the DNA sequence and controls the expression of the DNA sequence More specifically, examples of a combination of a DNA sequence derived from *Arabidopsis thaliana* and a phosphorus deficiency-responsive expression control sequence include a fused gene including a DNA sequence that encodes a DGAT1 gene of *Arabidopsis thaliana* and a sequence of a promoter of an MGD2 gene that is operably linked to the DNA sequence and controls the expression of the DNA sequence; a fused gene including a DNA sequence that encodes a DGAT2 gene of *Arabidopsis thaliana* and a sequence of a promoter of an MGD2 gene that is operably linked to the DNA sequence and controls the expression of the DNA sequence; a fused gene including a DNA sequence that encodes a DGAT3 gene of *Arabidopsis thaliana* and a sequence of a promoter of an MGD2 gene that is operably linked to the DNA sequence and controls the expression of the DNA sequence; a fused gene including a DNA sequence that encodes a DGAT4 gene of *Arabidopsis thaliana* and a sequence of a promoter of an MGD2 gene that is operably linked to the DNA sequence and controls the expression of the DNA sequence; a fused gene including a DNA sequence that encodes a PDAT gene of *Arabidopsis thaliana* and a sequence of a promoter of an MGD2 gene that is operably linked to the DNA sequence and controls the expression of the DNA sequence; a fused gene including a DNA sequence that encodes a DGAT1 gene of *Arabidopsis thaliana* and a sequence of a promoter of an MGD3 gene that is operably linked to the DNA sequence and controls the expression of the DNA sequence; a fused gene including a DNA sequence that encodes a DGAT2 gene of *Arabidopsis thaliana* and a sequence of a promoter of an MGD3 gene that is operably linked to the DNA sequence and controls the expression of the DNA sequence; a fused gene including a DNA sequence that encodes a DGAT3 gene of *Arabidopsis thaliana* and a sequence of a promoter of an MGD3 gene that is operably linked to the DNA sequence and controls the expression of the DNA sequence; a fused gene including a DNA sequence that encodes a DGAT4 gene of *Arabidopsis thaliana* and a sequence of a promoter of an MGD3 gene that is operably linked to the DNA sequence and controls the expression of the DNA sequence; and a fused gene including a DNA sequence that encodes a PDAT gene of *Arabidopsis thaliana* and a sequence of a promoter of an MGD3 gene that is operably linked to the DNA sequence and controls the expression of the DNA sequence.

Among these, the sequences relating to the promoter sequences of MGD2 and MGD3 genes are preferable because these sequences are extremely strongly induced in a phosphorus-deficient state. Furthermore, these sequences are preferable because they are control sequences that respond at a timing delayed from the beginning of the phosphorus-deficient state, and thus the growth process of the host plant is not easily affected by the sequences.

In the present invention and the present specification, the "stringent conditions" can be created by, for example, the method described in Molecular Cloning—A LABORATORY MANUAL THIRD EDITION (Sambrook et al, Cold Spring Harbor Laboratory Press). Examples thereof include conditions under which hybridization is performed by incubating for several hours or overnight at 55° C. to 70° C. in a hybridization buffer composed of 5×SSC (composition of 20×SSC: 3 M sodium chloride, 0.3 M citric acid solution, pH 7.0), 0.1% by weight N-lauroylsarcosine, 0.02% by weight SDS, and a 2% by weight blocking reagent for nucleic acid hybridization, and 50% formamide. A wash buffer used at the time of washing after incubation is preferably a 1×SSC solution containing 0.1% by weight SDS and more preferably a 0.1×SSC solution containing 0.1% by weight SDS.

The base sequence identity is calculated by, for example, a Lipman-Pearson method (Science, 227, 1435(1985)). Specifically, by using a homology analysis (Search Homology) program of genetic information processing software Genetyx-Win (Ver.5.1.1; Software Development), analysis is performed by setting Unit size to compare (ktup) to be 2, thereby calculating the base sequence identity. The amino acid sequence identity is calculated using, for example, a program of BLASTP provided from the National Center of Biotechnology Information (NCBI).

<<Vector>>

The vector of the present invention is not particularly limited as long as it contains the fused gene of the present invention. For example, the vector of the present invention may be prepared as an expression vector by using any expression vector which is generally used for constructing transgenic plant cells or transgenic plants, and incorporating relevant genes into the expression vector by a known gene recombination technique. Examples of the expression vector include binary vectors such as pBI121, pBI101, pCAMBIA, and GATEWAY.

The vector of the present invention may further have a sequence of any selection marker gene. The use of the selection marker gene makes it possible to easily select a plant in which the vector of the present invention is transformed and a plant in which it is not transformed. Examples of the selection marker gene include a hygromycin resistance gene, a kanamycin resistance gene, a bialaphos resistance gene, and the like.

According to the vector of the present invention, it is possible to provide a transgenic plant which can more efficiently manufacture vegetable fat or oil compared to a plant cultivated in a phosphorus-deficient state or a plant suffering from phosphorus deficiency known in the related art. Furthermore, the components of the manufactured vegetable fat or oil can be further improved compared to the original components thereof from the host.

<<Kit for Constructing Transgenic Plant>>

The kit for constructing a transgenic plant of the present invention includes the vector of the present invention. In addition to the vector of the present invention, the kit of the present invention may further include a solvent, a dispersion medium, a reagent, instructions for using these, and the like.

Herein, to "include" a solvent and the like means a state in which the solvent and the like are contained in any of the containers (for example, a bottle, a plate, a tube, a dish, and the like) constituting the kit. The "instructions" may be written or printed on paper or other media. Alternatively, the instructions may be recorded in a magnetic tape, a computer-readable disk or tape, or an electronic media such as a CD-ROM. Furthermore, the kit of the present invention may include containers containing a diluent, a solvent, a cleaning liquid, and other reagents.

<<Transgenic Plant and Method for Constructing Transgenic Plant>>

The transgenic plant of the present invention contains the fused genes of the present invention.

For constructing the transgenic plant of the present invention, the fused gene may be prepared before the transgenic plant is constructed, and the prepared fused gene may be introduced into a host such that the host contains the fused gene. Furthermore, for constructing the transgenic plant of the present invention, for example, in the vicinity of the "phosphorus deficiency-responsive expression control sequence" in a genome of a host, only the "nucleic acid sequence encoding a protein which affects the biosynthesis or accumulation of neutral lipid" may be introduced into the host such that the expression of the nucleic acid sequence is controlled, thereby preparing a fused gene. The fused gene of the present invention may be contained in the host in the aforementioned manner. Alternatively, for constructing the transgenic plant of the present invention, in the vicinity of the "nucleic acid sequence encoding a protein which affects the biosynthesis or accumulation of neutral lipid" in a genome of a host, only the "phosphorus deficiency-responsive expression control sequence" may be introduced into the host such that the expression of the nucleic acid sequence is controlled, thereby preparing a fused gene. The fused gene of the present invention may be contained in the host in the aforementioned manner. Examples of the above sequence introduction techniques include gene targeting.

The fused gene of the present invention has the phosphorus deficiency-responsive expression control sequence. Therefore, the transgenic plant of the present invention, in which the fused gene of the present invention is contained and thus the nucleic acid sequence affecting the biosynthesis or accumulation of neutral lipid is expressed due to the phosphorus deficiency-responsive expression control sequence, can favorably grow. The following can be considered as one of the reasons. A plant immediately after germination can grow by using a small amount of phosphorus, and after it grows to some extent, the plant tends to easily suffer from phosphorus deficiency. Accordingly, the phosphorus deficiency responsiveness tends to be induced after the plant grows to some extent and the tissue thereof fully grows. As a result, the induction of expression of the protein which affects the biosynthesis or accumulation of neutral lipid caused by the phosphorus deficiency-responsive expression control sequence does not easily affect the growth process of the host plant, for example. If a plant can favorably grow, vegetable fat or oil can be more efficiently manufactured. This is because fat or oil starts to be manufactured after the plant tissue as a place manufacturing fat or oil is formed in a favorably organized manner. It is considered that accordingly the function of manufacturing fat or oil is satisfactorily performed.

According to the phosphorus deficiency-responsive expression control sequence, it is possible to make a large amount of neutral lipid accumulate in tissue other than in seeds. In the related art, a method was tried in which a protein affecting the biosynthesis of neutral lipid having a special fatty acid composition is forcibly expressed in seeds so as to synthesize a large amount of neutral lipid having a special fatty acid composition in the seeds. However, in a case where the neutral lipid having a special fatty acid composition was excessively accumulated in seeds, fertility deteriorated in some cases depending on the type of the fatty acid, and this was not preferable for using the plant. In contrast, the method of manufacturing a large amount of neutral lipid in leaves by using the phosphorus deficiency-responsive expression control sequence does not easily affect the developmental process of a host plant in seeds and makes it possible to more efficiently manufacture vegetable fat or oil.

The transgenic plant of the present invention may be obtained by introducing the vector of the present invention into a host.

As long as the fused gene of the present invention is introduced into the host, "introducing the vector of the present invention into a host" may be the introduction of the entirety of the vector or the introduction of a partial nucleic acid sequence of the vector.

The type of the plant used in the present invention and the plant used as a host is not particularly limited as long as the plants are living organisms conducting photosynthesis. The same can be applied to various algae such as blue-green algae, red algae, diatoms, and green algae.

The plant used in the present invention and the plant used as a host are preferably terrestrial plants. From the viewpoint of growth speed, the obtained phytomass (biomass amount), and the like, it is preferable to use seed plants because they are advantageous to efficient production. Examples of the seed plants include angiosperms like a mono-cotyledonous plant such as Arecaceae or Gramineae and a dicotyledonous plant such as Leguminosae, Brassicaceae, Asteraceae, Euphorbiaceae, Pedaliaceae, Oleaceae, Lythraceae, Lamiaceae, Apiaceae, Chenopodiaceae, or Malvaceae, gymnosperms like Pinaceae and Ginkgoaceae, and the like.

Examples of more specific plant species include coco palms (*Cocos nucifera*), palms (*Elaeis guineensi* and *Elaeis oleifera*), and the like belonging to Arecaceae, rice (*Oryza sativa* and *Oryza glaberrima*), corn (*Zea mays*), miscanthus (*Miscanthus giganteus*), barnyard grass (*Echinochloa crusgalli*), and the like belonging to Gramineae, soybean (*Glycine max*) and the like belonging to Leguminosae, rape seeds (*Brassica rapa* and *Brassica napus*), *Arabidopsis thaliana*, *Camelina sativa*, Chinese cabbage (*Brassica rapa* var. *glabra*), cabbage (*Brassica oleracea* var. *capitata*), Komatsuna (*Brassica rapa* var. *peruviridis*), Mizuna (*Brassica rapa* var. *nipposinica*), watercress (*Nasturtium officinale*), and the like belonging to Brassicaceae, sunflower (*Helianthus annuus*), safflower (*Carthamus tinctorius*), lettuce (*Lactuca sativa*), and the like belonging to Asteraceae, castor seeds (*Ricinus communis*) and Jatropha (*Jatropha curcas*) belonging to Euphorbiaceae, sesame seeds (*Sesamum indicum*) and the like belonging to Pedaliaceae, olive (*Olea europea*) and the like belonging to Oleaceae, cuphea (*Cuphea hyssopifolia*) and the like belonging to Lythraceae, Aojiso (*Perilla frutescens* var. *cripsa*), Akajiso (*Perilla frutescen* var. *crispa*), basil (*Ocimum basilicum* L.), and the like belonging to Lamiaceae, Mitsuba (*Cryptotaenia japonica*), coriander (*Coriandrum sativum* L.), parsley (*Petroselium cripsum*), and the like belonging to Apiaceae, spinach (*Spinacia oleracea*) and the like belonging to Chenopodiaceae, and tobacco (*Nicotiana tabacum*), tomato (*Solanum lycopersicum* L.), and the like belonging to Solanaceae. Among these, angiosperms are preferable, dicotyledonous plants are more preferable, and plants belonging to Brassicaceae are even more preferable. Among these, *Arabidopsis thaliana*, tomato, rape seeds, barnyard grass, or tobacco is more preferable, and *Arabidopsis thaliana* is even more preferable.

As the method for introducing the vector of the present invention or the sequence included in the fused gene of the present invention into a plant, it is possible to use a known *agrobacterium* method, a particle gun method, an electroporation method, a polyethylene glycol (PEG) method, and the like.

As the plant material to which the vector of the present invention or the sequence included in the fused gene of the present invention is introduced, plant organs or plant tissues such as stems, leaves, seeds, embryo, ovule, ovary, shoot apex, anther, and pollen may be used, or plant culture cells may be used. In a case where plant tissues and the like are used as transgenic materials, for example, a method can be adopted in which callus is formed by dedifferentiating the plant tissues in a known callus-forming medium and then transplanted into a medium for inducing redifferentiation so as to obtain an adventitious embryo or an adventitious bud, and a transgenic plant is obtained therefrom.

The transgenic plant of the present invention includes plant cells or plants, into which the vector of the present invention or the sequence of the fused gene of the present invention is expressibly introduced, offspring of plants that have the same properties as the plants, or tissues derived from these.

Whether or not the vector of the present invention or the sequence included in the fused gene of the present invention has been introduced into a plant may be checked by a PCR method, a southern hybridization method, a northern hybridization method, and the like. Alternatively, it may be checked using the aforementioned selection marker gene. In a case where a reporter gene is used as the selection marker gene, the expression of the reporter gene in the plant can be used as a parameter. Furthermore, in a case where a drug resistance gene is used as the selection marker gene, a transgenic plant can be selected using the resistance to the drug as a parameter.

The transgenic plant of the present invention may be a plant in which at least one function selected from the group consisting of carbohydrate metabolism, starch biosynthesis, and membrane lipid metabolism is depressed or inhibited.

The host described above may be a plant in which at least one function selected from the group consisting of carbohydrate metabolism, starch biosynthesis, and membrane lipid metabolism is depressed or inhibited.

Examples of the plant in which the function of starch biosynthesis is depressed or inhibited include a plant in which the biosynthesis of starch is inhibited and the accumulation of starch in, for example, leaves is further depressed than in the original plant (wild type). Examples thereof include a plant in which the accumulation amount of starch in leaves is preferably decreased and becomes about 0% to 50% and more preferably becomes about 0% to 20% of the accumulation amount of starch in the wild type.

Examples of the method for obtaining the plant in which the biosynthesis of starch is inhibited include the inactivation of the function by causing a deletion or insertion mutation in structural genes of an enzyme which is involved in key steps of the biosynthesis of starch, that is, the generation of glucose-1-phosphate from glucose-6-phosphate, the generation of ADP glucose from glucose-1-phosphate, and the generation of starch from ADP glucose. The examples also include the inhibition (inactivation or the like) of gene expression by causing a deletion or insertion mutation in a domain involved in the expression of the genes.

Examples of the enzyme involved in the biosynthesis of starch include phosphoglucomutase (PGM) involved in the generation of glucose-1-phosphate from glucose-6-phosphate, ADP-glucose pyrophosphorylase (AGPase) involved in the generation of ADP glucose from glucose-1-phosphate, and starch synthase (SS) synthesizing starch from ADP glucose. Examples of the structural genes thereof include a PGM gene, an APL gene, an ADG gene, and a soluble glycogen synthase-related gene (see Japanese Unexamined Patent Application, First Publication No. 2012-153833). Specific examples of the plant include an adg1-1 mutant and an aps1 mutant of *Arabidopsis thaliana* in which the functions of the ADG gene are inactivated and inhibited respectively.

The plant in which the "function of membrane lipid metabolism" is depressed or inhibited refers to a plant in which the function involved in the reduction of the amount of a precursor substance for the biosynthesis of neutral lipid in the membrane lipid metabolism is depressed or inhibited.

In a plant suffering from phosphorus deficiency, by using phospholipid-derived phosphorus in the plant, the metabolic pathway runs such that glycolipid is synthesized as an alternative to phospholipid, and as a result, phosphatidylcholine (PC) as a precursor substance of TAG is converted into diacylglycerol (DAG) and then into glycolipid (digalactosyldiacylglycerol, DGDG). Therefore, examples of the method for obtaining the plant in which the function of the membrane lipid metabolism is depressed or inhibited include the inactivation of the function by causing a deletion or insertion mutation in the structural genes of an enzyme such as PLD, which is an enzyme involved in the conversion of PC into DAG and then DGDG, and the inhibition (inactivation or the like) of the gene expression by causing a deletion or insertion mutation in a domain involved in the expression of the genes.

Examples of the method for causing a deletion mutation in the genes and in the base sequence of the domain of the expression control sequence thereof and the like include a method of using a mutation-inducing agent such as ethyl methanesulfonate or nitrosoguanidine and a method of performing irradiation of γ rays and the like. From a group of random mutants generated by these deletion methods, mutants in which the intended function is depressed or inhibited should be selected.

Examples of the method of causing an insertion mutation in the genes and in the base sequence of the domain of the expression control sequence thereof and the like include the insertion of a T-DNA domain on a Ti plasmid by an *agrobacterium* transformation method, a method of using a transposon, and the like. From a group of random mutants generated by these insertion methods, mutants in which the intended function is depressed or inhibited should be selected.

The transgenic plant of the present invention may be a plant obtained by the hybridization between a transgenic plant containing the fused gene of the present invention or a transgenic plant that becomes a host into which the vector of the present invention is introduced and a plant in which at least one function selected from the group consisting of carbohydrate metabolism, starch biosynthesis, and membrane lipid metabolism is depressed or inhibited.

For example, a transgenic plant may be obtained by introducing the vector of the present invention into a wild-type plant used as a host and then hybridized with any plant in which at least one function selected from the group of carbohydrate metabolism, starch biosynthesis, and membrane lipid metabolism is depressed or inhibited, thereby obtaining a transgenic plant which has the vector of the present invention and in which the aforementioned function is depressed or inhibited.

As described above, by depressing or inhibiting at least one function selected from the group consisting of carbohydrate metabolism, starch biosynthesis, and membrane lipid metabolism in the transgenic plant of the present invention, the amount of fat or oil accumulated in the plant can be markedly increased, and vegetable fat or oil can be efficiently manufactured.

<<Method for Manufacturing Vegetable Fat or Oil>>

The method for manufacturing vegetable fat or oil of the present invention includes a cultivation step of cultivating the transgenic plant of the present invention.

At the time of recovering fat or oil manufactured by the method for manufacturing vegetable fat or oil of the present invention, it is preferable to recover the fat or oil from the transgenic plant of the present invention including fully grown tissue.

The "transgenic plant including fully grown tissue" means a plant in which the plant tissue of root, stems, leaves, and the like have been fully grown under normal conditions. That is, in a case where the plant is germinated from a seed, the transgenic plant including fully grown tissue means a plant which has grown to such a degree that rooting or two or more foliage leaves are observed. Preferred examples of the transgenic plant including fully grown tissue include a plant which is cultivated in a medium containing an appropriate amount of phosphorus, and includes grown plant tissue of root, stems, leaves, and the like, and has a sufficient phytomass (biomass amount), that is, a plant which has been so grown that the weight thereof becomes 10 times or more of the weight of the seed.

At the time of recovering fat or oil manufactured by the method for manufacturing vegetable fat or oil of the present invention, it is preferable to recover neutral lipid accumulated in tissue other than seeds because the biomass amount of the tissue is great. The tissue other than seeds is more preferably leaves because the producible biomass amount thereof is extremely great.

The method for manufacturing vegetable fat or oil of the present invention preferably further includes a step of cultivating the transgenic plant of the present invention in a phosphorus-deficient state.

Examples of the step of "cultivating in a phosphorus-deficient state" include 1) a step of cultivating a plant including fully grown tissue by transplanting it into a phosphorus-deficient medium, 2) a step of cultivating the plant by replacing the medium thereof with a phosphorus-deficient medium, 3) a step of cultivating the plant while maintaining a phosphorus-deficient state that can be created in the medium in the process of cultivation, and the like.

The medium used for cultivation is not limited in any of the growth stages of the plant and the accumulation stage of fat or oil, and it is possible to use soil, a water culture medium (culture solution), a solid medium, and the like. Furthermore, any of outdoor sunlight, artificial indoor lighting, and the like can be used, and the amount of light or the irradiation time is not particularly limited. However, it is desirable to use optimal conditions unique to the plant.

The "phosphorus-deficient state" means a state where the medium does not contain phosphorus or contains phosphorus at an extremely low concentration. Specifically, from the viewpoint of promoting the accumulation of neutral lipid, it is desirable that the phosphorus concentration in the medium be close to zero. In a case where the phosphorus concentration is not zero, it is preferably less than 1/30, more preferably equal to or less than 1/100, even more preferably equal to or less than 1/300, and particularly preferably equal to or less than 1/1,000 of the concentration of phosphorus used in general cultivation.

For example, in a case where the plant is hydroponically cultivated using the medium shown in Table 1 or cultivated using an agar medium, the phosphorus concentration of the medium containing phosphorus at an extremely low concentration is preferably less than 33 µM, more preferably equal to or less than 10 µM, even more preferably equal to or less than 3.3 µM, particularly preferably equal to or less than 1 µM, and most preferably equal to or less than 0.33 µM.

The method for manufacturing vegetable fat or oil of the present invention preferably further includes a step of cultivating the transgenic plant of the present invention as a plant suffering from phosphorus deficiency.

The "mutant plant suffering from phosphorus deficiency" means, for example, a mutant plant in which the phosphorus concentration is reduced because the transport of phosphorus or the like is hindered. The state where the transport of phosphorus is hindered means, for example, a state in which genes involved in phosphorus transport have a problem, and examples of the mutant include pho1 and pho2 of *Arabidopsis thaliana* (reference: Journal of Plant Physiology (1991) Vol. 97, p. 1087). Even if such a mutant plant is not cultivated in a phosphorus-deficient state, that is, even if such a mutant plant is in a medium containing phosphorus, the accumulation of neutral lipid is promoted in the plant.

The cultivation in the phosphorus-deficient state should be performed at a normal temperature, humidity, and pH and under normal light irradiation conditions. The duration of the cultivation in the phosphorus-deficient state is not particularly limited. However, in view of the accumulation of neutral lipid, the plant is cultivated preferably for several days to several weeks, particularly preferably for 3 days to 3 weeks, and most preferably for 1 to 2 weeks.

For example, in a case where *Arabidopsis thaliana* is used as the plant, it should be cultivated under the conditions of 18° C. to 25° C., light intensity of 30 µE/cm$^2$ to 70 µE/cm$^2$, and irradiation time of 6 hrs/day to 24 hrs/day.

The method for preparing the medium used for the cultivation in the phosphorus-deficient state is not particularly limited. As the medium, soil which is generally called phosphorus-deficient soil, for example, soil which contains soluble phosphoric acid in an amount of equal to or less than 100 mg/100 g and preferably in an amount of equal to or less than 50 mg/100 g can be used. Furthermore, the medium can be prepared by applying a phosphorus-free fertilizer such as an NK chemical fertilizer to the aforementioned soil or by applying a fertilizer which is obtained by adding a phosphorus fertilizer such as a small amount of phosphoric acid to a phosphorus-free fertilizer such as an NK chemical fertilizer to the aforementioned soil. In a case where a water culture medium or a solid medium is used, it is possible to use a culture solution or a medium obtained by appropriately formulating necessary nutrients other than phosphorus. The necessary nutrients other than phosphorus are not particularly limited and can include potassium nitrate, ammonium nitrate, ammonium sulfate, calcium nitrate, sodium nitrate, potassium chloride, calcium chloride, magnesium sulfate, sodium sulfate, iron (III) sulfate, iron (III) chloride, iron (III) sulfate, disodium ethylenediaminetetraacetate, sodium iron ethylenediaminetetraacetate, manganese sulfate, zinc sulfate, boric acid, copper sulfate, sodium molybdate, molybdenum trioxide, potassium iodide, cobalt chloride, aluminum chloride, nickel chloride, myo-inositol, thiamine hydrochloride, pyridoxine hydrochloride, nicotinic acid, folic acid, biotin, glycine, and the like. A gelling agent of the solid medium is not particularly limited, and agar, gelatin, Gelrite (manufactured by Wako Pure Chemical Industries, Ltd.), and the like can be used.

As an embodiment of the cultivation in the "phosphorus-deficient state", for example, a plant including fully grown tissue grown in an MS medium (Physiologia Plantarum (1962) Vol. 15, p. 473) is cultivated by being transplanted into a medium having the composition shown in Table 1 or by replacing the MS medium with a phosphorus-free medium shown in Table 1. Alternatively, for example, a plant is further cultivated for several days to several weeks in a phosphorus-free state or in a state where the phosphorus concentration is extremely low, for instance, in a state where the phosphorus concentration is preferably less than 33 µM, more preferably equal to or less than 10 µM, even more preferably equal to or less than 3.3 µM, particularly preferably equal to or less than 1 µM, and most preferably equal to or less than 0.33 µM.

TABLE 1

Composition of phosphorus-containing medium or phosphorus-free medium

| Composition | Concentration Phosphorus-containing medium | Phosphorus-free medium |
| --- | --- | --- |
| KNO$_3$ | 2.5 mM | 2.5 mM |
| Ca(NO$_3$)$_2$ 4H$_2$O | 1 mM | 1 mM |
| MgSO$_4$ 7H$_2$O | 1 mM | 1 mM |
| H$_3$BO$_3$ | 35 µM | 35 µM |
| MnCl$_2$ 4H$_2$O | 7 µM | 7 µM |
| CuSO$_4$ 5H$_2$O | 0.25 µM | 0.25 µM |
| ZnSO$_4$ 7H$_2$O | 0.5 µM | 0.5 µM |
| Na$_2$MoO$_4$ 2H$_2$O | 0.1 µM | 0.1 µM |
| CoCl$_2$ 6H$_2$O | 0.005 µM | 0.005 µM |
| NaCl | 5 µM | 5 µM |
| Fe-EDTA | 25 µM | 25 µM |
| KH$_2$PO$_4$ | 1 mM | 0 mM |
| MES buffer solution | 20 mM | 20 mM |
| Sucrose | 1% | 1% |
| Agar | 0.8% | 0.8% |
| pH | 6 | 6 |

As another embodiment, for example, a plant is cultivated in a state where the phosphorus-deficient state created in the process of cultivation is maintained. In this case, after the plant is cultivated for an appropriate period of time, and thus the phosphorus concentration becomes extremely low, the cultivation should be further continued for several days to several weeks. The initial phosphorus concentration in the medium used in this case should be adjusted such that the phosphorus concentration in the medium becomes extremely low as described above or becomes zero after the plant is fully grown.

The method for recovering neutral lipid accumulated in the root, leaves, stems, or the like of the plant is not particularly limited. For example, vegetable fat or oil can be obtained by a method of pulverizing or squeezing the root, leaves, stems, and the like of the plant or by a method of extracting the vegetable fat or oil by using an appropriate solvent. More specifically, for example, by using a method of pulverizing the root, leaves, stems, or the like of the plant and then extracting vegetable fat or oil by normal hexane, a method such as a Bligh and Dyer method (Can. J. Biochem. Physiol. (1959) Vol. 37, p. 911), or the like, vegetable fat or oil can be efficiently extracted, and neutral lipid can be recovered in the form of being contained in the vegetable fat or oil. The vegetable fat or oil can be directly used as neutral lipid or can be used after a purification treatment such as degumming, deoxidizing, bleaching, and deodorizing, and the treatment method is not particularly limited. Furthermore, neutral lipid can be separated-recovered from the vegetable fat or oil, and the method thereof is not particularly limited. More specifically, examples thereof include separation by thin-layer chromatography, recovery from a silica gel plate, separation-collection using high-performance liquid chromatography, and the like.

By cultivating the transgenic plant of the present invention in a phosphorus-deficient state or by cultivating the transgenic plant of the present invention as a plant suffering from phosphorus deficiency, the amount of fat or oil accumulated in the plant can be further increased. Into the transgenic plant of the present invention, the vector "containing a nucleic acid sequence which affects the biosynthesis or accumulation of neutral lipid and a phosphorus deficiency-responsive expression control sequence which is operably linked to the aforementioned nucleic acid sequence and controls the expression of the nucleic acid sequence" is introduced. Therefore, by cultivating the transgenic plant of the present invention in the aforementioned state or cultivating the transgenic plant of the present invention as the aforementioned plant, fat or oil can be extremely efficiently manufactured by using the phosphorus-deficient conditions.

EXAMPLES

Next, the present invention will be more specifically explained by describing examples, but the present invention is not limited to the following examples.

<Selecting Protein Affecting Biosynthesis of Nutral Lipid>

In a case where the "nucleic acid sequence which affects the biosynthesis or accumulation of neutral lipid" included in the fused gene of the present invention encodes a protein which affects the biosynthesis or accumulation of neutral lipid, as the protein, various proteins can be selected. However, it is considered that among the proteins affecting the biosynthesis of neutral lipid, DGAT or PDAT1 exerts a great influence because these proteins are involved in the final stage of the TAG synthesis. Furthermore, from the viewpoint of further increasing the amount of the manufactured fat or oil, the conditions under which the DGAT or PDAT1 may affect the amount of the synthesized TAG were investigated.

As a plant known to particularly increase the accumulation amount of TAG in a phosphorus-deficient state, there is a pgm-1 mutant strain of *Arabidopsis thaliana*. The pgm-1 mutant strain is a mutant strain in which the function of a gene having an AGI code of At5g51820 is impaired due to mutation, and thus the carbohydrate metabolism and starch biosynthesis are hindered. The expression amount of mRNA of the DGAT1 gene, the DGAT2 gene, and the PDAT1 gene in the pgm-1 mutant strain and a wild strain was measured as below.

(Expression Analysis)

Figure 1B:
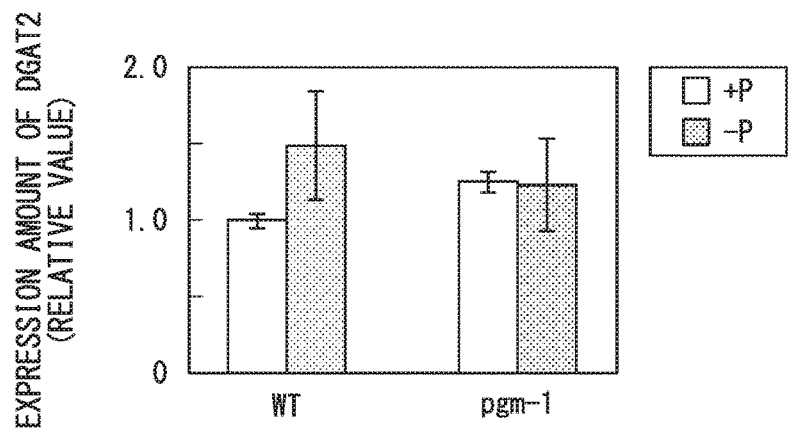
FIG. 1B is a graph showing the expression amount (relative value) of a DGAT2 gene of an *Arabidopsis thaliana* wild strain and a pgm-1 mutant strain cultivated using a medium not containing soluble phosphoric acid and a medium containing 1 mM soluble phosphoric acid.
Figure 1C:
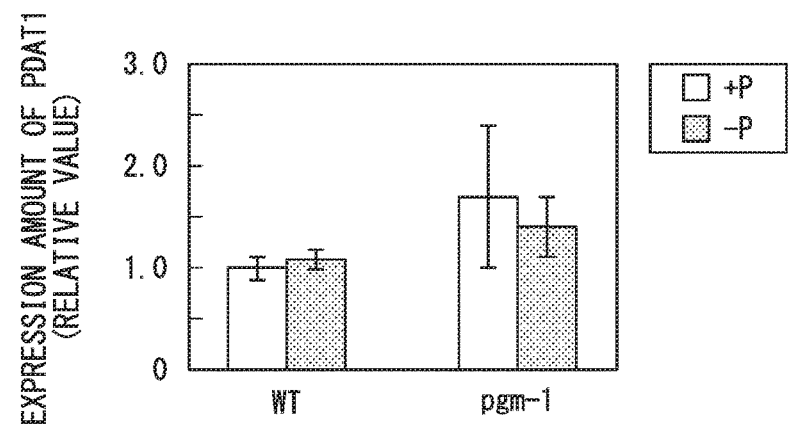
FIG. 1C is a graph showing the expression amount (relative value) of a PDAT1 gene of an *Arabidopsis thaliana* wild strain and a pgm-1 mutant strain cultivated using a medium not containing soluble phosphoric acid and a medium containing 1 mM soluble phosphoric acid.

Forty seeds of each of the Col-0 strain (wild strain) and the pgm-1 mutant strain of *Arabidopsis thaliana* were seeded into an MS agar medium (Physiologia Plantarum (1962) Vol. 15, p. 473) and cultivated for 10 days under conditions of 22° C., light intensity of 40 µE/cm$^2$ to 70 µE/cm$^2$, and irradiation time of 24 hrs/day. The grown plants were removed with great care from the MS agar medium, and 20 individual plants of each strain were transplanted into the medium shown in Table 1 in which the concentration of soluble phosphoric acid ($KH_2PO_4$) was 0 mM. Furthermore, as a control group, 20 individual plants were transplanted into the medium shown in Table 1 containing 1 mM soluble phosphoric acid and cultivated for 10 days under the same conditions as described above. The cultivated plants were removed from the agar medium, and the above-ground part thereof was cut off. After the weight of the above-ground part was measured, the above-ground part was pulverized using a mortar in liquid nitrogen, and RNA was extracted using an SV Total RNA Isolation System (manufactured by Promega Corporation). Then, by using a PrimeScript RT reagent kit (manufactured by TAKARA BIO INC.), a reverse transcription reaction was performed, thereby obtaining cDNA of total mRNA. By using the obtained cDNA and a Thermal Cycler Dice Real Time System (TP800, manufactured by TAKARA BIO INC.), real-time PCR was performed. At this time, SYBR PreMix Ex Taq (manufactured by TAKARA BIO INC.) was used as a reagent. The amount of a transcription product of interest was corrected based on the expression amount of mRNA of the ubiquitin-10 gene, thereby relativizing the expression amount of mRNA of each of the DGAT1 gene, the DGAT2 gene, and the PDAT1 gene. FIGS. 1A to 1C show the relative values of the expression amount of mRNA of the DGAT1 gene, the DGAT2 gene, and the PDAT1 gene in the wild strain and the pgm-1 mutant strain cultured under the conditions of normal phosphorus concentration (1 mM, indicated by +P) or under the phosphorus-deficient conditions (0 Mm, indicated by −P). FIGS. 1A, 1B, and 1C show the measured results of the expression amount of the DGAT1 gene, the DGAT2 gene, and the PDAT1 gene respectively. From the results shown in FIGS. 1A to 1C, it is understood that in the pgm-1 mutant strain known to particularly increase the accumulation amount of TAG in phosphorus-deficient conditions, under any of the conditions of normal phosphorus concentration and the phosphorus-deficient conditions, the expression amount of each of the DGAT1 gene, the DGAT2 gene, and the PDAT1 gene is the same as that of the wild strain.

<Preparation of Vector>

As described above, the inventors of the present invention obtained knowledge that in the plant cultivated in a phosphorus-deficient state, even if the amount of triacylglycerol (TAG) per plant is increased, the expression amount of the gene which encodes acyltransferase causing a reaction of converting an acyl group into a diacylglycerol (DAG) skeleton as a final stage of TAG biosynthesis is the same as the expression amount thereof in the wild-type plant. Based on the knowledge, the inventors assumed that by controlling the expression of the gene involved in the TAG synthesis pathway in the plant cultivated in the phosphorus-deficient state or in the plant suffering from phosphorus deficiency, more TAG may be able to be accumulated in the plant tissue. Based on the assumption, the inventors prepared the following vectors.

Example 1-1

First, from total RNA extracted from leaves of the wild strain of *Arabidopsis thaliana*, cDNA was obtained by RT-PCR. Thereafter, by using a primer 1-1F: 5'-CGC-CCGGGTATGGCGATTTTGGATTCTGCTGGC-3' (SEQ ID NO: 19) and a primer 2-1: 5'-GCGAGCTCTCAT-GACATCGATCCTTTTCGGTTC-3' (SEQ ID NO: 20), the sequence was amplified, thereby obtaining a base sequence encoding the DGAT1 gene. Then, the base sequence was cloned into a pMD20 cloning vector (TAKARA BIO INC.), and by using Quikchange lightning reaction (QIAGEN), a SacI cleavage site in the sequence was modified. As a result, a modified sequence including a base sequence encoding the DGAT1 gene was obtained.

An atMGD3::GUS/pBI101 vector including a base sequence of a promoter of the MGD3 gene represented by SEQ ID NO: 12 was obtained by the method described in Kobayashi et al. 2004 Plant Phys. By using a DNA Ligation Kit (Mighty Mix) (manufactured by TAKARA BIO INC.), the modified sequence including the base sequence encoding the DGAT1 gene was linked to the site of SmaI/SacI on the binary vector atMGD3::GUS/pBI101 through a ligation reaction. As a result, a vector of Example 1-1 having the base sequence of the promoter of the MGD3 gene and the base sequence encoding the DGAT1 gene was obtained.

The vector of Example 1-1 was introduced into an *agrobacterium* GV3101 strain.

Example 1-2

From total RNA extracted from leaves of the wild strain of *Arabidopsis thaliana*, cDNA was obtained by RT-PCR. Thereafter, by using a primer 1-2: 5'-GCCCCGGG-TATGGGTGGTTCCAGAGAGTTCCGAG-3' (SEQ ID NO: 27) and a primer 2-2: 5'-GCGAGCTCT-CAAAGAATTTTCAGCTCAAGATC-3' (SEQ ID NO: 28), the sequence was amplified, thereby obtaining a base sequence encoding the DGAT2 gene. Then, in the same manner as in Example 1-1, a vector of Example 1-2 having the base sequence of the promoter of the MGD3 gene and the base sequence encoding the DGAT2 gene was obtained.

The vector of Example 1-2 was introduced into the *agrobacterium* GV3101 strain.

Example 1-3

From total RNA extracted from leaves of the wild strain of *Arabidopsis thaliana*, cDNA was obtained by RT-PCR. Thereafter, by using a primer 1-3: 5'-CGCCCGGGTATGC-CCCTTATCATCGGAAAAAG-3' (SEQ ID NO: 29) and a primer 2-3: 5'-GCGAGCTCTCACAGCTTCAGGT-CAATACGCTC-3' (SEQ ID NO: 30), the sequence was amplified, thereby obtaining a base sequence encoding the PDAT1 gene. Then, in the same manner as in Example 1-1, a vector of Example 1-3 having the base sequence of the promoter of the MGD3 gene and the base sequence encoding the PDAT1 gene was obtained.

The vector of Example 1-3 was introduced into the *Agrobacterium* GV3101 strain.

<Preparation of Transgenic Plant>

Example 2-1

The wild strain of *Arabidopsis thaliana* was cultivated, and by a Floral dip method (see document, Clough et al., Plant Journal (1998) 16: 735-743), the vector of Example 1-1 was introduced into the plant from *Agrobacterium* holding the vector of Example 1-1. As a result, a transgenic plant of Example 2-1 having the base sequence of the promoter of the MGD3 gene and the base sequence encoding the DGAT1 gene was obtained.

Example 2-2

The wild strain of *Arabidopsis thaliana* was cultivated, and the vector of Example 1-2 was introduced into the plant in the same manner as in Example 2-1. As a result, a transgenic plant of Example 2-2 having the base sequence of the promoter of the MGD3 gene and the base sequence encoding the DGAT2 gene was obtained.

Example 2-3

The wild strain of *Arabidopsis thaliana* was cultivated, and the vector of Example 1-3 was introduced into the plant in the same manner as in Example 2-1. As a result, a transgenic plant of Example 2-3 having the base sequence of the promoter of the MGD3 gene and the base sequence encoding the PDAT1 gene was obtained.

Example 3-1

The pgm-1 mutant strain was cultivated, and the vector of Example 1-1 was introduced into the plant in the same manner as in Example 2-1. As a result, a transgenic plant of Example 3-1 was obtained which had the base sequence of the promoter of the MGD3 gene and the base sequence encoding the DGAT1 gene and in which the function of a PGM gene was impaired.

Example 3-2

The pgm-1 mutant strain was cultivated, and the vector of Example 1-2 was introduced into the plant in the same manner as in Example 2-1. As a result, a transgenic plant of Example 3-2 was obtained which had the base sequence of the promoter of the MGD3 gene and the base sequence encoding the DGAT2 gene and in which the function of the PGM gene was impaired.

Example 3-3

The pgm-1 mutant strain was cultivated, and the vector of Example 1-3 was introduced into the plant in the same manner as in Example 2-1. As a result, a transgenic plant of Example 3-3 was obtained which had the base sequence of the promoter of the MGD3 gene and the base sequence encoding the PDAT1 gene and in which the function of the PGM gene was impaired.

(Confirmation of Expression of DGAT1 Gene in Transgenic Plant)

Figure 2A:
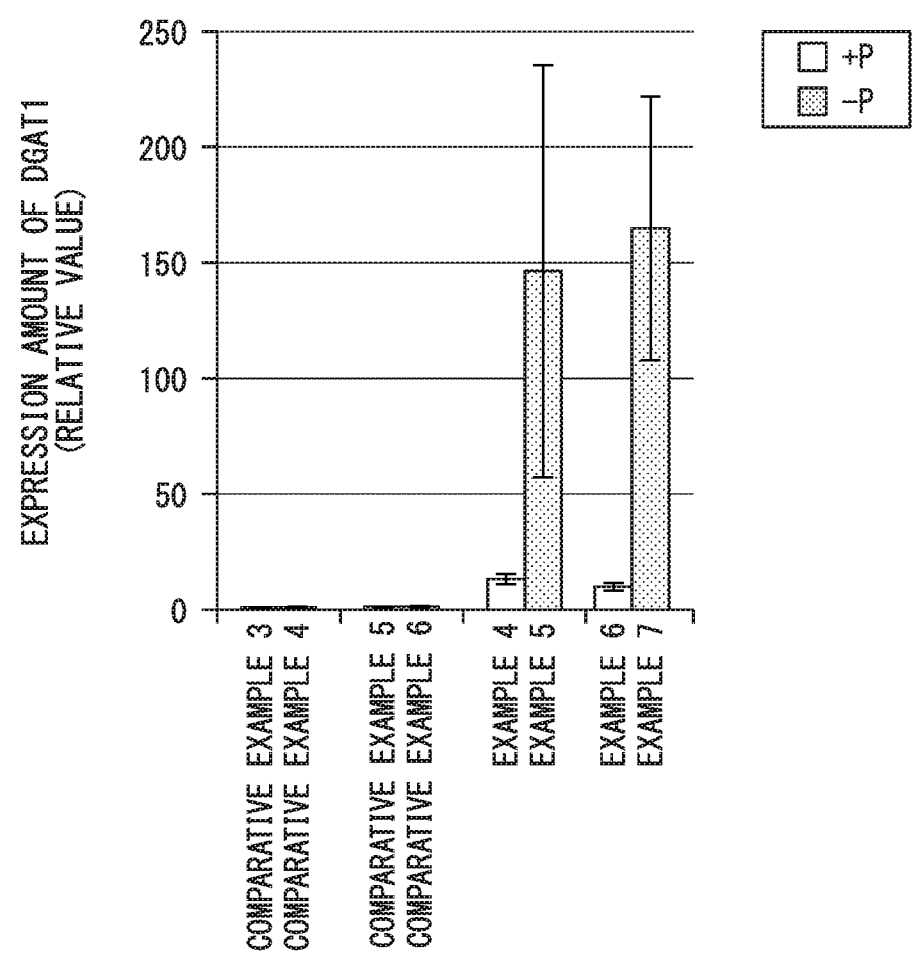
FIG. 2A is a graph showing the expression amount (relative value) of a DGAT1 gene in each of plants in Comparative examples 3 to 6 and Examples 4 to 7 under cultivation conditions using a medium not containing soluble phosphoric acid and a medium containing 1 mM soluble phosphoric acid.
Figure 2B:
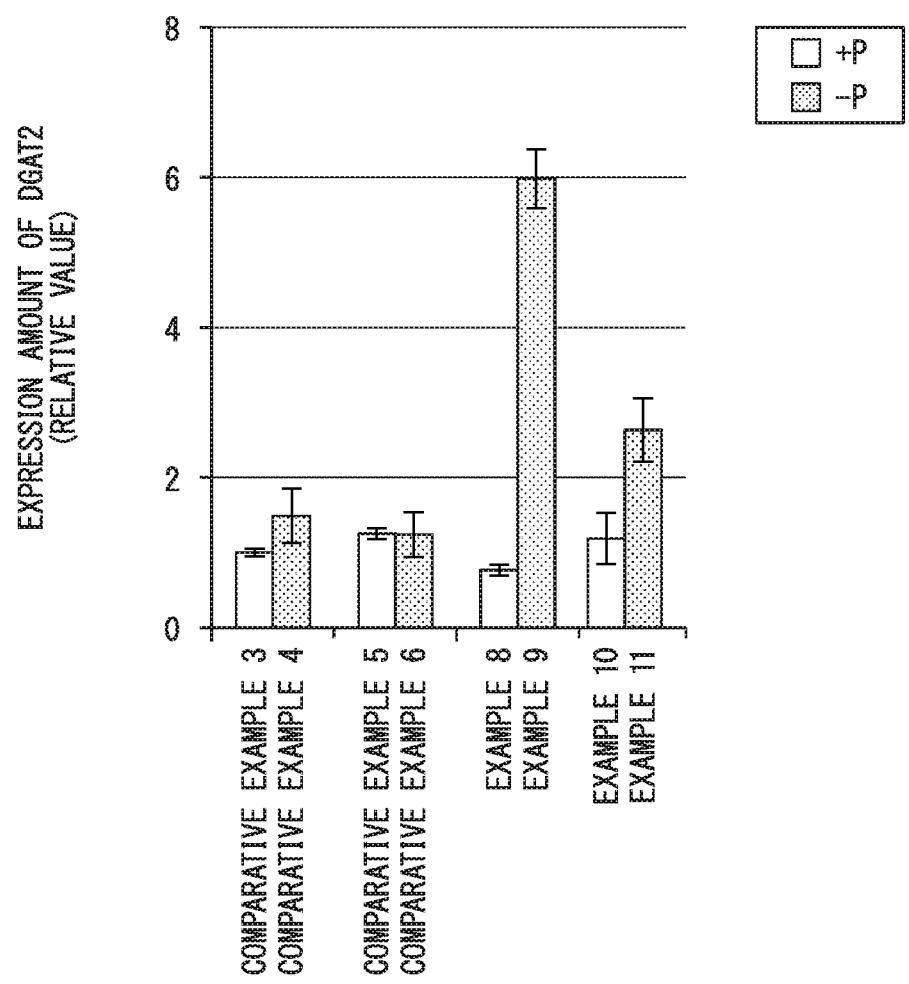
FIG. 2B is a graph showing the expression amount (relative value) of a DGAT2 gene in each of plants in Comparative examples 3 to 6 and Examples 8 to 11 under cultivation conditions using a medium not containing soluble phosphoric acid and a medium containing 1 mM soluble phosphoric acid.
Figure 2C:
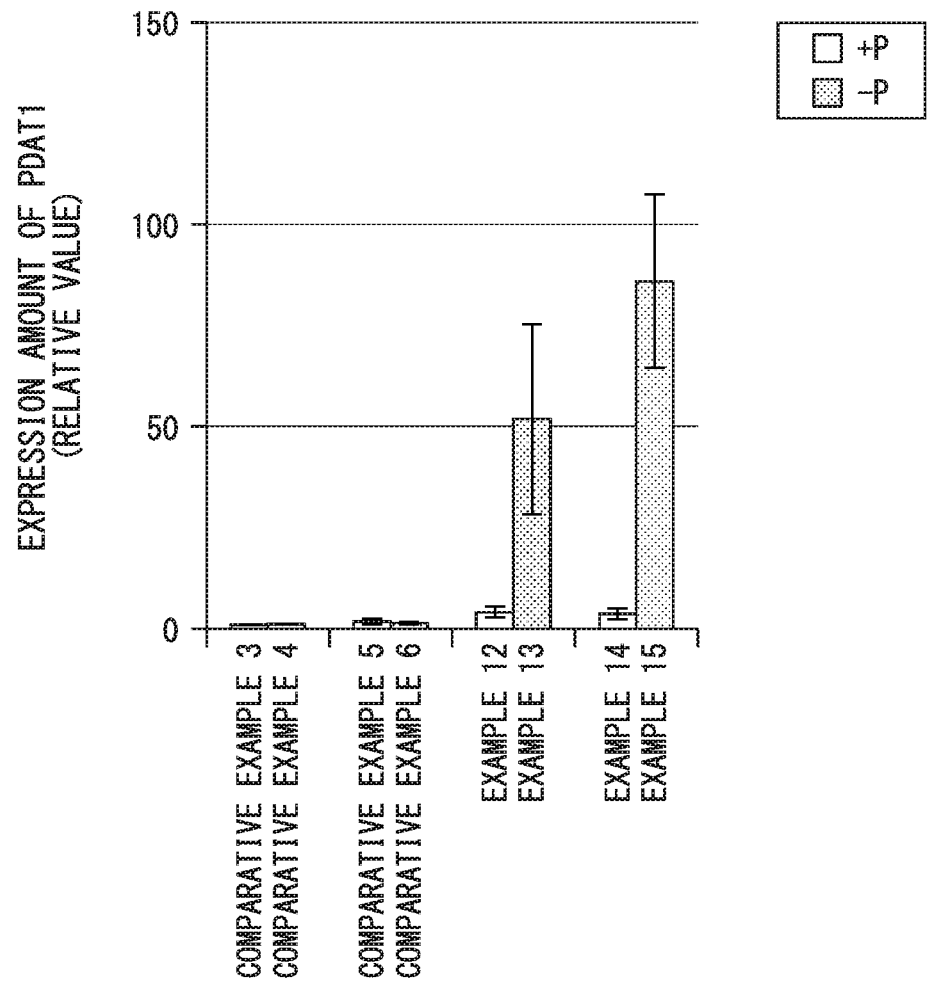
FIG. 2C is a graph showing the expression amount (relative value) of a PDAT1 gene in each of plants in Comparative examples 3 to 6 and Examples 12 to 15 under cultivation conditions using a medium not containing soluble phosphoric acid and a medium containing 1 mM soluble phosphoric acid.

In the same manner as used in the expression analysis of the DGAT1 gene, the expression amount of the DGAT1 gene in the transgenic plants of Examples 2-1 and 3-1 was determined; the expression amount of the DGAT2 gene in the transgenic plants of Examples 2-2 and 3-2 was determined; and the expression amount of the PDAT1 gene in the transgenic plants in Examples 2-3 and 3-3 was determined. The results are shown in FIGS. 2A to 2C. From the results, it could be confirmed that in the transgenic plants of Examples 2-1 to 2-3 and Examples 3-1 to 3-3, the expression of each of the DGAT1 gene, the DGAT2 gene, and the DAT1 gene was controlled and increased in response to phosphorus deficiency.

<Manufacturing Fat or Oil>

Example 4

Twenty seeds of the transgenic plant of Example 2-1 were seeded into an MS agar medium and cultivated for 10 days under conditions of 22° C., light intensity of 40 µE/cm² to 70 µE/cm², and irradiation time of 24 hrs/day. The grown plants were removed with great care from the MS agar medium. Thereafter, 20 individuals of the plants were transplanted into the medium shown in Table 1 in which the concentration of soluble phosphoric acid ($KH_2PO_4$) was 1 mM and further cultivated for 10 days under the same conditions as described above.

Example 5

Twenty seeds of the transgenic plant of Example 2-1 were seeded into an MS agar medium and cultivated for 10 days under conditions of 22° C., light intensity of 40 µE/cm² to 70 µE/cm², and irradiation time of 24 hrs/day. Thereafter, 20 individuals of the plants were transplanted into the medium shown in Table 1 in which the concentration of soluble phosphoric acid was 0 mM, and further cultivated for 10 days under the same conditions as described above.

Example 6

Twenty seeds of the transgenic plant of Example 3-1 were cultivated under the same conditions as in Example 4.

Example 7

Twenty seeds of the transgenic plant of Example 3-1 were cultivated under the same conditions as in Example 5.

Example 8

Twenty seeds of the transgenic plant of Example 2-2 were cultivated under the same conditions as in Example 4.

Example 9

Twenty seeds of the transgenic plant of Example 2-2 were cultivated under the same conditions as in Example 5.

Example 10

Twenty seeds of the transgenic plant of Example 3-2 were cultivated under the same conditions as in Example 4.

Example 11

Twenty seeds of the transgenic plant of Example 3-2 were cultivated under the same conditions as in Example 5.

Example 12

Twenty seeds of the transgenic plant of Example 2-3 were cultivated under the same conditions as in Example 4.

Example 13

Twenty seeds of the transgenic plant of Example 2-3 were cultivated under the same conditions as in Example 5.

Example 14

Twenty seeds of the transgenic plant of Example 3-3 were cultivated under the same conditions as in Example 4.

Example 15

Twenty seeds of the transgenic plant of Example 3-3 were cultivated under the same conditions as in Example 5.

Comparative Example 1

Twenty seeds of the wild strain were seeded into an MS agar medium and cultivated for 10 days under conditions of 22° C., light intensity of 40 μE/cm² to 70 μE/cm², and irradiation time of 24 hrs/day. The grown plants were removed with great care from the MS agar medium. Thereafter, twenty individuals of the plants were transplanted into the medium shown in Table 2 in which the nitrogen (N) concentration was 4.5 mM (normal), and further cultivated for 10 days under the same conditions as described above.

Comparative Example 2

Twenty seeds of the wild strain were seeded into an MS agar medium and cultivated for 10 days under conditions of 22° C., light intensity of 40 μE/cm² to 70 μE/cm², and irradiation time of 24 hrs/day. The grown plants were removed with great care from the MS agar medium. Thereafter, twenty individuals of the plants were transplanted into the medium shown in Table 2 in which the nitrogen (N) concentration was 0 mM, and further cultivated for 10 days under the same conditions as described above.

Comparative Example 3

Twenty seeds of the wild strain were cultivated by the same method and under the same conditions as in Example 4.

Comparative Example 4

Twenty seeds of the wild strain were cultivated by the same method and under the same phosphorus-deficient conditions as in Example 5.

Comparative Example 5

Twenty seeds derived from the pgm-1 mutant strain into which none of the vectors of Examples 1-1 to 1-3 were introduced were cultivated by the same method and under the same conditions as in Example 4.

Comparative Example 6

Twenty seeds derived from the pgm-1 mutant strain into which none of the vectors of Examples 1-1 to 1-3 were introduced were cultivated by the same method and under the same phosphorus-deficient conditions as in Example 5.

TABLE 2

Composition of nitrogen-containing medium and nitrogen-free medium

| Composition | Nitrogen-containing medium | Nitrogen-free medium |
| --- | --- | --- |
| $KNO_3$ | 2.5 mM | 0 mM |
| $Ca(NO_3)_2\ 4H_2O$ | 1 mM | 0 mM |
| $MgSO_4\ 7H_2O$ | 1 mM | 1 mM |
| $H_3BO_3$ | 35 μM | 35 μM |
| $MnCl_2\ 4H_2O$ | 7 μM | 7 μM |
| $CuSO_4\ 5H_2O$ | 0.25 μM | 0.25 μM |
| $ZnSO_4\ 7H_2O$ | 0.5 μM | 0.5 μM |
| $Na_2MoO_4\ 2H_2O$ | 0.1 μM | 0.1 μM |
| $CoCl_2\ 6H_2O$ | 0.005 μM | 0.005 μM |
| NaCl | 5 μM | 5 μM |
| Fe-EDTA | 25 μM | 25 μM |
| $KH_2PO_4$ | 1 mM | 1 mM |
| MES buffer solution | 20 mM | 20 mM |
| Sucrose | 1% | 1% |
| Agar | 0.8% | 0.8% |
| pH | 6 | 6 |

Table 3 shows the plant of each example used for manufacturing fat or oil.

TABLE 3

| | Arabidopsis thaliana | Fused gene | Cultivation conditions (composition of medium) |
| --- | --- | --- | --- |
| Example 4 | WT | MGD3-DGAT1 | Normal |
| Example 5 | WT | MGD3-DGAT1 | -Pi |
| Example 6 | pgm-1 | MGD3-DGAT1 | Normal |
| Example 7 | pgm-1 | MGD3-DGAT1 | -Pi |
| Example 8 | WT | MGD3-DGAT2 | Normal |
| Example 9 | WT | MGD3-DGAT2 | -Pi |
| Example 10 | pgm-1 | MGD3-DGAT2 | Normal |
| Example 11 | pgm-1 | MGD3-DGAT2 | -Pi |
| Example 12 | WT | MGD3-PDAT1 | Normal |
| Example 13 | WT | MGD3-PDAT1 | -Pi |
| Example 14 | pgm-1 | MGD3-PDAT1 | Normal |
| Example 15 | pgm-1 | MGD3-PDAT1 | -Pi |
| Comparative example 1 | WT | — | Normal |
| Comparative example 2 | WT | — | -N |
| Comparative example 3 | WT | — | Normal |
| Comparative example 4 | WT | — | -Pi |
| Comparative example 5 | pgm-1 | — | Normal |
| Comparative example 6 | pgm-1 | — | -Pi |

(Measurement of Fresh Weight of Plant)

Figure 3:
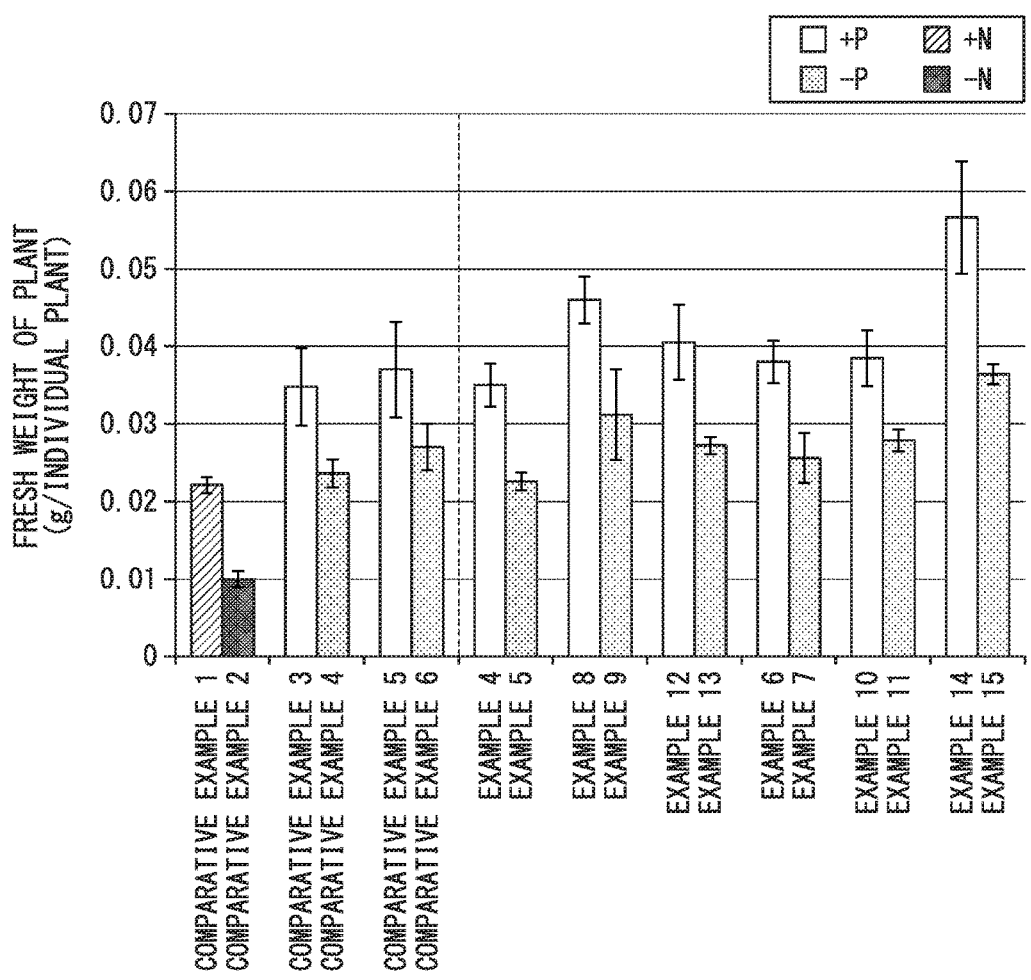
FIG. 3 is a graph showing a fresh weight of an individual plant in Examples 4 to 15 and Comparative examples 1 to 6.

Each of the plants cultivated for manufacturing fat or oil in Comparative examples 1 to 6 and each of the transgenic plants cultivated for manufacturing fat or oil in Examples 4 to 15 were removed from the agar medium after cultivation and cut into above-ground parts (leaves and stems) and roots. Thereafter, the weight of the above-ground parts was measured (for 20 individuals). The results are shown in FIG. 3.

Through the comparison between Comparative examples 1 and 2 and Comparative examples 3 and 4, it was understood that the plants grow better when cultivated under the phosphorus-deficient conditions than under the nitrogen-deficient conditions. Furthermore, from the comparison between Examples 4 to 15 and Comparative examples 3 to 6, it was confirmed that the growth of the transgenic plants of Examples 4 to 15 into which any of the vectors of Examples 1-1 to 1-3 was introduced is as excellent as the growth of the wild strain and the pgm-1 mutant strain into which none of the vectors of Examples 1-1 to 1-3 were introduced.

(Measurement of Accumulation Amount of Fat or Oil in Plant)

The components of fat or oil in the plant tissue were analyzed by the following method.

(1) Extraction and Pretreatment

The total lipid was extracted based on a Bligh and Dyer method (Can. J. Biochem. Physiol. (1959) Vol. 37, p. 911). From the total lipid, TAG was separated by thin-layer chromatography (TLC Silica gel 60, 20×20 cm, Merck &

Co., Inc., product code 1.05721.0009, composition of developing solvent: hexane:diethylether:acetic acid=160:40:4 (vol/vol)). By collecting the segregated spots of TAG from the plate, the content was measured.

(2) Measurement of Amount of Neutral Lipid

TAG was subjected to a methanolysis treatment with using a 15:0 fatty acid as an internal standard sample. Specifically, in a screw-capped glass test tube, 100 µl of 1 mM 15:0 hexane solution (pentadecanoic acid, Sigma-Aldrich Co. LLC., P-6125) and 350 µl of a 5% hydrogen chloride-methanol solution (Wako Pure Chemical Industries, Ltd., 089-03971) were added to silica gel powder containing TAG, and the resultant was treated for 1 hour at 85° C. After the methanolysis treatment, fatty acid methyl ester was recovered using hexane and dried and solidified in nitrogen gas. Then, the resultant was recovered using 60 µl of hexane, and 3 µl of the resultant was analyzed by gas chromatography. By gas chromatography (Shimadzu Corporation, GC-2014, column: ULBON HR-SS-10 (25 m, 0.25 mm ID) from Shinwa Chemical Industries Ltd., column temperature: 180° C., temperature of gasification chamber and detector: 250° C., inlet pressure (kPa): 68.2, flow rate of column (ml/min): 0.53, split ratio: 68.8, measurement time: 15 min), separation-quantification were performed.

(3) Measurement of Dry Weight of Plant Tissue

After the plants were subjected to a freeze-drying treatment for 20 hours, the weight thereof was measured, thereby obtaining a dry weight.

Figure 4:
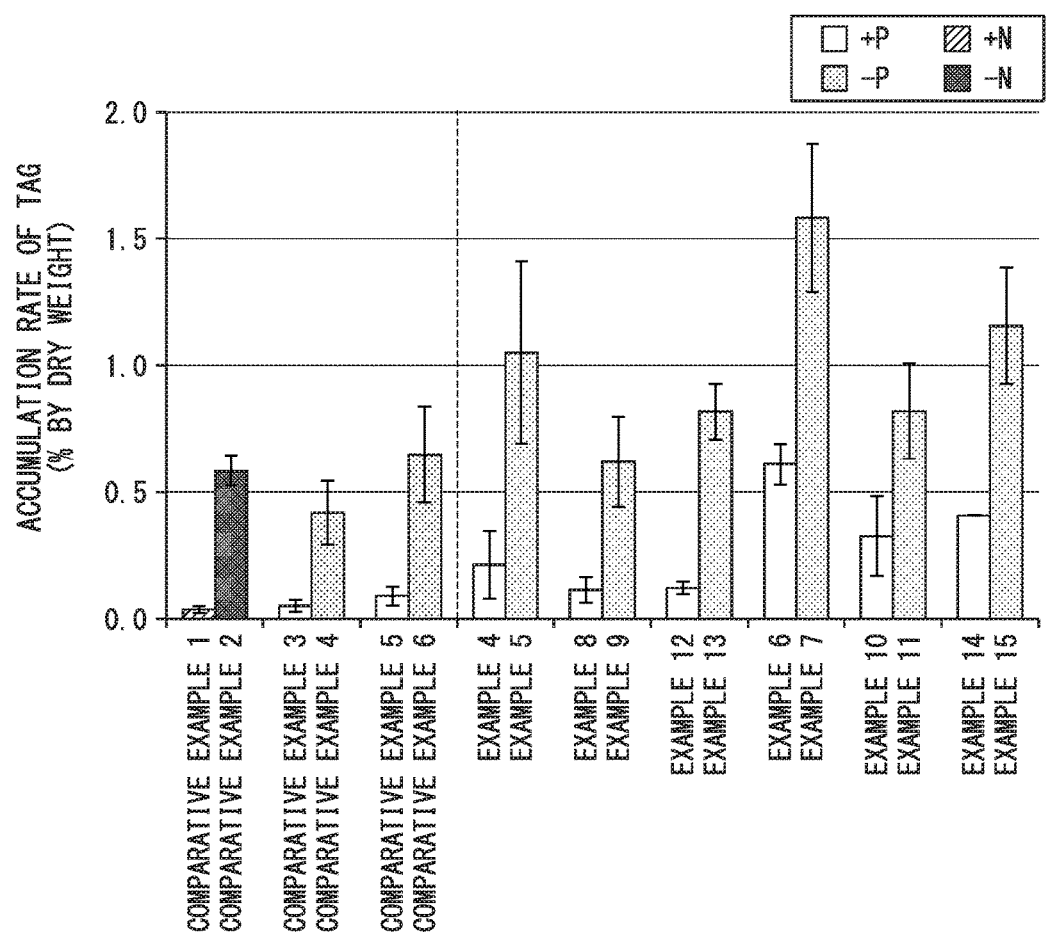
FIG. 4 is a graph showing an accumulation rate of TAG per dry weight of a plant in Examples 4 to 15 and Comparative examples 1 to 6.
Figure 5:
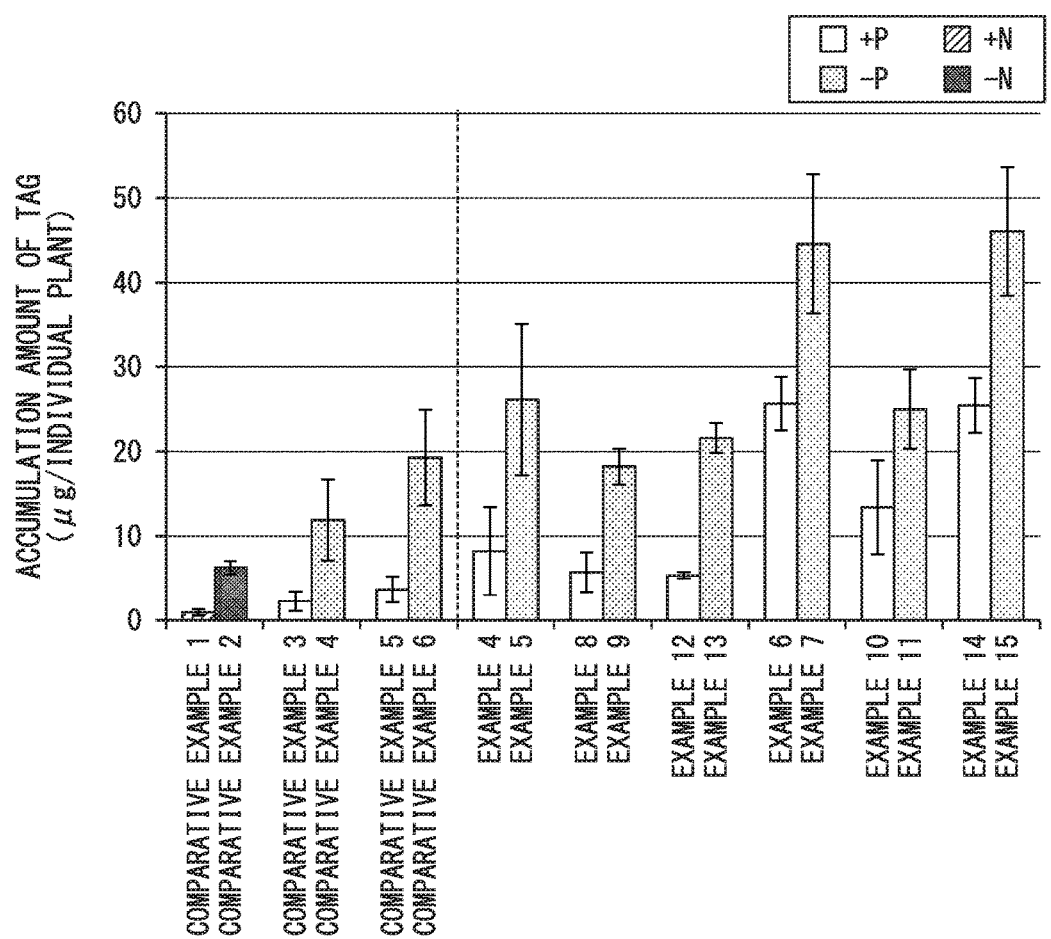
FIG. 5 is a graph showing an accumulation amount of TAG per fresh weight of a plant in Examples 4 to 15 and Comparative examples 1 to 6.

Each of the plants cultivated for manufacturing fat or oil in Comparative examples 1 to 6 and each of the transgenic plants cultivated for manufacturing fat or oil in Examples 4 to 15 were removed from the agar medium after cultivation and cut into above-ground parts (leaves and stems) and root. The above-ground parts were pulverized using a mortar in liquid nitrogen, and fat was extracted by the Bligh and Dyer method described above (20 individuals for each plant). Thereafter, TAG was separated-purified by thin-layer chromatography. Then, TAG was subjected to a methanolysis treatment by using methanol and hydrochloride, and lipid analysis was performed using gas chromatography. FIG. 4 shows a ratio (% by weight) of TAG amount per individual plant (dry weight). FIG. 5 shows the TAG amount per individual plant (fresh weight).

As shown in FIGS. 4 and 5, it is understood that in a case where the plant is cultivated under the phosphorus-deficient conditions, the accumulation of fat or oil can be further improved while the growth of the plant is being favorably maintained, than in a case where the plant is cultivated under the nitrogen-deficient conditions.

As shown in FIG. 4, in the leaves and stems of the transgenic plant in Example 4, the effect of improving TAG accumulation was about 4 times stronger than in the wild strain in Comparative example 3.

In the leaves and stems of the transgenic plant in Example 8, the effect of improving TAG accumulation was about 2 times stronger than in the wild strain in Comparative example 3.

In the leaves and stems of the transgenic plant in Example 12, the effect of improving TAG accumulation was about 2 times stronger than in the wild strain in Comparative example 3.

In the leaves and stems of the transgenic plant in Example 5, the effect of improving TAG accumulation was about 2.5 times stronger than in the wild strain in Comparative example 4 and about 20 times stronger than in the wild strain in Comparative example 3.

In the leaves and stems of the transgenic plant in Example 9, the effect of improving TAG accumulation was about 1.3 times stronger than in the wild strain in Comparative example 4 and about 7 times stronger than in the wild strain in Comparative example 3.

In the leaves and stems of the transgenic plant in Example 13, the effect of improving TAG accumulation was about 2 times stronger than in the wild strain in Comparative example 4 and about 10 times stronger than in the wild strain in Comparative example 3.

The above results clearly show that in the transgenic plants in which each of the DGAT1 gene, the DGAT2 gene, and the PDAT1 gene is expressed by the phosphorus deficiency-responsive promoter sequence, the TAG accumulation in the plant can be improved, and the TAG accumulation can be greatly improved by cultivating the transgenic plants in a phosphorus-deficient state.

As shown in FIG. 4, in the leaves and stems of the transgenic plant in Example 6, the effect of improving TAG accumulation was about 10 times stronger than in the wild strain in Comparative example 3 and about 7 times stronger than in the pgm-1 mutant strain in Comparative example 5.

In the leaves and stems of the transgenic plant in Example 10, the effect of improving TAG accumulation was about 6.5 times stronger than in the wild strain in Comparative example 3 and about 3.5 times stronger than in the pgm-1 mutant strain of Comparative example 5.

In the leaves and stems of the transgenic plant in Example 14, the effect of improving TAG accumulation was about 8 times stronger than in the wild strain in Comparative example 3 and about 4.5 times stronger than in the pgm-1 mutant strain of Comparative example 5.

In the leaves and stems of the transgenic plant in Example 7, the effect of improving TAG accumulation was about 4 times stronger than in the wild strain in Comparative example 4 and about 2.5 times stronger than in the pgm-1 mutant strain in Comparative example 6.

In the leaves and stems of the transgenic plant in Example 11, the effect of improving TAG accumulation was about 2 times stronger than in the wild strain in Comparative example 4 and about 1.1 times stronger than in the pgm-1 mutant strain in Comparative example 6.

In the leaves and stems of the transgenic plant in Example 15, the effect of improving TAG accumulation was about 3.5 times stronger than in the wild strain in Comparative example 4 and about 2 times stronger than in the pgm-1 mutant strain in Comparative example 6.

In the leaves and stems of the transgenic plant in Example 7, the effect of improving TAG accumulation was about 30 times stronger than in the wild strain in Comparative example 3 and about 17 times stronger than in the pgm-1 mutant strain in Comparative example 5.

In the leaves and stems of the transgenic plant in Example 11, the effect of improving TAG accumulation was about 12 times stronger than in the wild strain in Comparative example 3 and about 7 times stronger than in the pgm-1 mutant strain in Comparative example 5.

In the leaves and stems of the transgenic plant in Example 15, the effect of improving TAG accumulation was about 19 times stronger than in the wild strain in Comparative example 3 and about 11 times stronger than in the pgm-1 mutant strain in Comparative example 5.

From the above results, it was confirmed that in the transgenic plants in which any of the DGAT1 gene, the DGAT2 gene, and the PDAT1 gene is expressed by the phosphorus deficiency-responsive promoter sequence, by depressing the functions of carbohydrate metabolism and starch biosynthesis, the TAG accumulation in the plants can also be further improved, and the TAG accumulation can be markedly improved by cultivating the transgenic plants in a phosphorus-deficient state.

Each of the constituents, combinations thereof, and the like in each of the aforementioned embodiments is merely an example. Within a scope that does not depart from the gist of the present invention, the constituents can be added, omitted, or substituted and may be modified in other ways. Furthermore, the present invention is not limited to each of the embodiments but limited by only the scope of claims.

INDUSTRIAL APPLICABILITY

According to the present invention, it is possible to obtain a transgenic plant which makes it possible to efficiently manufacture vegetable fat or oil while continuing photosynthesis of the plant. The transgenic plant of the present invention is useful because the plant makes it possible to particularly efficiently manufacture vegetable fat or oil especially when the plant is cultivated under phosphorus-deficient conditions such as the cultivation in phosphoric acid-deficient soil. Therefore, the transgenic plant makes a contribution to the utilization of phosphorus-deficient soil which is increasing all over the world, including Asia, is unsuitable for the growth of crops and the like, and thus becomes problematic in terms of agricultural utilization. Furthermore, it is possible to provide a new method which can manufacture a large amount of fat or oil by using leaves of plants that have not been generally used for producing fat or oil.

In addition, the properties of the generated fat or oil can be freely modified, and by manufacturing fat or oil composed of fatty acids used for fuel having high market prices, the industrial applicability thereof can be further widened.

The invention claimed is:

1. A fused gene, comprising:
a nucleic acid sequence encoding a diacylglycerol acyltransferase (DGAT) or a phospholipid diacylglycerol acyltransferase (PDAT) which increases the synthesis of a plant neutral lipid; and a phosphorus deficiency-responsive promoter of a monogalactosyldiacylglycerol (MGDG) synthase gene which is operably linked to the nucleic acid sequence and controls expression of the nucleic acid sequence.

2. The fused gene according to claim 1,
Wherein the protein which increases the synthesis of a plant neutral lipid is a protein comprising an amino acid sequence which shares identity equal to or greater than 90% with the amino acid sequence represented by any of SEQ ID NOs: 1 to 5 and has acyltransferase activity.

3. A vector comprising the fused gene according to claim 1.

4. A transgenic plant comprising the fused gene according to claim 1.

5. A transgenic plant obtained by introducing the vector according to claim 3 into a host.

6. The transgenic plant according to claim 4 that is a plant in which at least one function selected from the group consisting of carbohydrate metabolism, starch biosynthesis, and membrane lipid metabolism is depressed or inhibited.

7. A transgenic plant obtained by the hybridization between the transgenic plant according to claim 4 and a plant in which at least one function selected from the group consisting of carbohydrate metabolism, starch biosynthesis, and membrane lipid metabolism is depressed or inhibited.

8. A method for manufacturing vegetable fat or oil, comprising:
a cultivation step of cultivating the transgenic plant according to claim 4.

9. The method for manufacturing vegetable fat or oil according to claim 8,
wherein the cultivation step is a step of cultivating the transgenic plant in a phosphorus-deficient state.

10. The method for manufacturing vegetable fat or oil according to claim 9,
wherein the cultivating in the phosphorus-deficient state is a step of cultivating a plant including fully grown tissue by transplanting the plant into a phosphorus-deficient medium, by replacing a medium of the plant with a phosphorus-deficient medium, or by maintaining the phosphorus-deficient state that is created in a medium in the process of cultivation.

11. The method for manufacturing vegetable fat or oil according to claim 8,
wherein the cultivation step is a step of cultivating the transgenic plant as a plant suffering from phosphorus deficiency.

12. The method for manufacturing vegetable fat or oil according to claim 11,
wherein the plant suffering from phosphorus deficiency is a plant in which a function of transporting phosphoric acid is depressed or inhibited.

13. A method for constructing a transgenic plant, comprising:
a step of introducing the vector according to claim 3 into a plant.

14. A kit for constructing a transgenic plant, comprising: the vector according to claim 3.

* * * * *